United States Patent
Bar-Tana

(10) Patent No.: US 10,479,752 B2
(45) Date of Patent: Nov. 19, 2019

(54) DEUTERATED TETRAMETHYL DIOIC ACIDS, COMPOSITIONS COMPRISING THEM AND USES THEREOF

(71) Applicant: SYNDROMEX LTD., Jerusalem (IL)

(72) Inventor: Jacob Bar-Tana, Jerusalem (IL)

(73) Assignee: SYNDROMEX LTD., Jerusalem (IL)

( * ) Notice: Subject to any disclaimer, the term of this patent is extended or adjusted under 35 U.S.C. 154(b) by 120 days.

(21) Appl. No.: 14/363,912

(22) PCT Filed: Dec. 6, 2012

(86) PCT No.: PCT/IL2012/050511
§ 371 (c)(1),
(2) Date: Jun. 9, 2014

(87) PCT Pub. No.: WO2013/084237
PCT Pub. Date: Jun. 13, 2013

(65) Prior Publication Data
US 2014/0371314 A1 Dec. 18, 2014

Related U.S. Application Data

(60) Provisional application No. 61/568,441, filed on Dec. 8, 2011.

(51) Int. Cl.
| | |
|---|---|
| *C07C 55/02* | (2006.01) |
| *C07C 69/34* | (2006.01) |
| *C07C 67/32* | (2006.01) |
| *C07C 67/347* | (2006.01) |
| *C07C 51/02* | (2006.01) |
| *C07C 51/09* | (2006.01) |
| *C07C 51/41* | (2006.01) |
| *C07B 59/00* | (2006.01) |
| *A61K 9/10* | (2006.01) |
| *A61K 47/38* | (2006.01) |

(52) U.S. Cl.
CPC ............... *C07C 55/02* (2013.01); *A61K 9/10* (2013.01); *A61K 47/38* (2013.01); *C07B 59/001* (2013.01); *C07C 51/02* (2013.01); *C07C 51/09* (2013.01); *C07C 51/41* (2013.01); *C07C 67/32* (2013.01); *C07C 67/347* (2013.01); *C07C 69/34* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,634,795 A | 1/1987 | Bar-Tana | |
| 4,711,896 A | 12/1987 | Bar-Tana et al. | |
| 4,908,385 A | 3/1990 | Bar-Tana et al. | |
| 6,284,903 B1 * | 9/2001 | Bar-Tana | C07C 69/602 554/121 |
| 6,303,653 B1 * | 10/2001 | Bar-Tana | A61K 31/00 514/527 |
| 2002/0037876 A1 | 3/2002 | Bar-Tana | |
| 2002/0049345 A1 | 4/2002 | Bar-Tana | |
| 2009/0018199 A1 | 1/2009 | Bar-Tana et al. | |

FOREIGN PATENT DOCUMENTS

| | | |
|---|---|---|
| EP | 0081930 A1 | 6/1983 |
| WO | 2012028106 A1 | 3/2012 |

OTHER PUBLICATIONS

Sanderson, K. Big Interest in Heavy Drugs. Nature. Mar. 16, 2009 (doi:10.1038/458269a).*
Harbeson, SL and Tung, RD. Deuterium in drug discovery and development. Chapter 24, pp. 403-418, in Annual Reports in Medicinal Chemistry, vol. 46 (2011).*
Buteau, KC. Deuterated drugs: unexpectedly nonobvious? 10 J. High Tech. L. 22 (2009).*
Precision deuterium chemistry backgrounder. Concert Pharmaceuticals, Inc. (2007).*
Blake et al. Studies with deuterated drugs. J. Pharm. Sci. 64(3), pp. 367-391 (1975).*
Cleland, WW. The use of isotope effects to determine enzyme mechanisms. Arch. Biochem. Biophys. 433, pp. 2-12 (2005).*
Shao, L. and Hewitt, MC. The kinetic isotope effect in the search for deuterated drugs. Drug News Persp. 23(6), pp. 398-404 (2010).*
STN Entry RN# 97543-02-7 entered Aug. 10, 1985 (Year: 1985).*
STN Entry RN# 72532-93-5 entered Nov. 16, 1984 (Year: 1984).*
Gutman et al "Deuterium NMR of perdeuteriated di and monoacids dissolved in the lyomesophases of dipotassium hexadecanedioate" Liquid Crystals. 8 (1) 31-46 (1990).
Zimmermann "Specifically denteriated intermediates for the synthesis of liquid crystals and liquid-crystalline polymers" Liquid Crystals. 4 (6) 591-618 (1989).

\* cited by examiner

*Primary Examiner* — Jeffrey S Lundgren
*Assistant Examiner* — Michael J Schmitt
(74) *Attorney, Agent, or Firm* — Browdy and Neimark, PLLC

(57) ABSTRACT

This invention relates to deuterated tetramethyl dioic acids, compositions comprising them and uses thereof in the treatment of Metabolic Syndrome and any diseases, disorders or symptoms associated therewith.

25 Claims, 3 Drawing Sheets

DEUTERATED TETRAMETHYL DIOIC ACIDS, COMPOSITIONS COMPRISING THEM AND USES THEREOF

FIELD OF THE INVENTION

This invention relates to deuterated tetramethyl dioic acids, compositions comprising them and uses thereof in the treatment of Metabolic Syndrome and any diseases, disorders or symptoms associated therewith.

BACKGROUND OF THE INVENTION

U.S. Pat. No. 4,634,795 discloses long-chain alpha, omega-di-carboxylic acids and derivatives for the treatment of obesity, hyperlipidemia and maturity-onset diabetes. US2002049345 discloses carboxylic acids and derivatives thereof, compositions comprising them for the treatment of obesity, hyperlipidemia and maturity onset diabetes. US2009018199 discloses methods for administering 3,3,14,14-tetramethyl hexadecane-1,16-dioic acid for lowering LDL, VLDL, total cholesterol, triglycerides, insulin resistance and hypertension, and methods for elevating HDL in subjects in need thereof. U.S. Pat. No. 4,908,385 provides a pharmaceutical composition containing at least one alpha-halogenated dicarboxylic acid. U.S. Pat. No. 4,711,896 relates to alpha, omega-dicarboxylic acids and uses thereof as anti-diabetic agents and for lowering the level of plasma lipids. US2002037876 relates to carboxylic acids and derivatives thereof for use in the treatment of metabolic syndrome X.

Isotopes are atoms which have nearly identical properties but which have different masses due to changes in the number of neutrons in their nuclei. Deuterium is an isotope of hydrogen with a nucleus comprising one neutron and one proton. Kinetic isotope effects are the observed changes in the rate of reaction that occur when deuterium is substituted for hydrogen. Deuterium isotope effects result from the greater energy required to break a covalent bond to deuterium versus a covalent bond to hydrogen. One of the challenges of incorporating deuterium into a pharmaceutical composition is the possibility of deuterium/hydrogen exchange within the physiological environment, eviscerating the effect of the compound. Further, when deuterium retards metabolism at one site, "metabolic shunting" can occur where the suppression of one metabolic pathway promotes metabolism at another site.

SUMMARY OF THE INVENTION

The present invention provides a compound of general formula (I), including any salts, esters, anhydrides or prodrugs thereof:

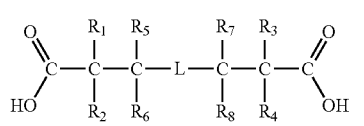

(I)

wherein

L is a straight or branched $C_8$-$C_{16}$ alkylene; optionally interrupted by at least one moiety selected from O, S, NH, $C_5$-$C_{10}$ cycloalkylene, $C_5$-$C_{10}$ cycloheteroalkylene, $C_6$-$C_{18}$ arylene, $C_6$-$C_{18}$ heteroarylene;

each of $R_1$-$R_8$ is independently selected from H, D, $CH_3$ and $CD_3$; wherein at least one of $R_1$-$R_8$ is D or $CD_3$.

In a compound of the invention, when a particular position is designated as having deuterium, it is understood that the abundance of deuterium at that position is substantially greater than the natural abundance of deuterium, which is 0.015%. A position designated as having deuterium typically has a minimum isotopic enrichment factor that is at least 3340 times greater than the natural abundance of deuterium (i.e., the term "D" or "deuterium" indicates at least 50.1% incorporation of deuterium).

The term "isotopic enrichment factor" as used herein means the ratio between the isotopic abundance and the natural abundance of a specified isotope.

In other embodiments, a compound of the invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In compounds of the invention any atom not specifically designated as a particular isotope is meant to represent the naturally abundant isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater (i.e., at least 50.1% incorporation of deuterium) than the natural abundance of deuterium, which is 0.015%.

The term "isotopologue" refers to a species that has the same chemical structure and formula as a specific compound of this disclosure, with the exception of the positions of isotopic substitution and/or level of isotopic enrichment at one or more positions, e.g., H vs. D.

The term "compound" as used herein includes a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure.

The relative amount of such isotopologues in a compound of this disclosure will depend upon a number of factors including the isotopic purity of deuterated reagents used to make the compound and the efficiency of incorporation of deuterium in the various synthesis steps used to prepare the compound.

In some embodiments, as set forth above, the relative amount of such isotopologues in total will be less than 49.9% of the compound. In other embodiments, the relative amount of such isotopologues in total will be less than 47.5%, less than 40%, less than 32.5%, less than 25%, less than 17.5%, less than 10%, less than 5%, less than 3%, less than 1%, or less than 0.5% of the compound.

The term "stable compounds" as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

In some embodiments, any position in the compound of Formula (I) designated as having D has a minimum deuterium incorporation of at least 50.1% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula (I). Thus, in some embodiments, a composition comprising a compound of Formula (I) can include a distribution of isotopologues of the compound, provided at least 50.1% of the isotopologues include a D at the designated position(s).

In some embodiments, a compound of Formula (I) is "substantially free of" other isotopologues of the compound, e.g., less than 49.9%, less than 25%, less than 10%, less than 5%, less than 2%, less than 1%, or less than 0.5% of other isotopologues are present.

The term "$C_8$-$C_{16}$ alkylene" is meant to encompass a straight or branched divalent (wherein two hydrogen atoms are removed from the corresponding alkyl) aliphatic hydrocarbon group having between 8 to 16 carbon atoms, which is optionally interrupted (i.e. in between any two carbon atoms of said alkylene group) by at least one moiety selected from —O—, —S—, —NH—, $C_5$-$C_{10}$ cycloalkylene (i.e. divalent cycloalkane ring), $C_5$-$C_{10}$ cycloheteroalkylene (i.e. divalent heterocycloalkane ring), $C_6$-$C_{18}$ arylene (i.e. divalent aryl ring), $C_6$-$C_{18}$ heteroarylene (i.e. divalent heteroaryl ring).

In another aspect the invention provides a compound of general formula (I), including any salts, esters, anhydrides or prodrugs thereof:

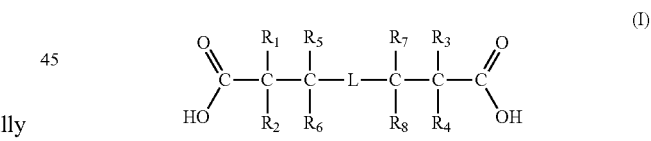

wherein

L is a straight or branched $C_8$-$C_{16}$ alkylene; optionally interrupted by at least one moiety selected from O, S, NH, $C_5$-$C_{10}$ cycloalkylene, $C_5$-$C_{10}$ cycloheteroalkylene, $C_6$-$C_{18}$ arylene, $C_6$-$C_{18}$ heteroarylene;

each of $R_1$-$R_4$ is independently H or D;

each of $R_5$-$R_8$ is independently $CH_3$ or $CD_3$;

wherein when $R_1$-$R_4$ are H, at least one of $R_5$-$R_8$ is $CD_3$; or when $R_5$-$R_8$ are $CH_3$, at least one of $R_1$-$R_4$ is D.

Thus, according to the first aspect of the application, at least one of the substituents $R_1$-$R_8$ comprises a deuterium atom. In some embodiments, at least one of $R_1$-$R_4$ is D and each of $R_5$-$R_8$ is independently $CH_3$ or $CD_3$. In other embodiments, at least one of $R_5$-$R_8$ is $CD_3$ and each of $R_1$-$R_4$ is independently H or D. In further embodiments $R_5$-$R_8$ are $CH_3$, and at least one of $R_1$-$R_4$ is D.

In some embodiments of a compound of the invention, at least one of said $R_1$-$R_4$ is D. In further embodiments, at least one of $R_5$-$R_8$ is $CD_3$. In yet other embodiments, at least one of $R_1$-$R_4$ is D and at least one of $R_5$-$R_8$ is $CD_3$.

In some embodiments, a compound of the invention is selected from:

| Compound | $R_1 = R_2 = R_3 = R_4$ | $R_5 = R_6 = R_7 = R_8$ |
|---|---|---|
| II | D | $CH_3$ |
| III | H | $CD_3$ |
| IV | D | $CD_3$ |

In other embodiments, a compound of the invention is selected from:

| Compound | $R_1 = R_2$ | $R_3 = R_4$ | $R_5 = R_6$ | $R_7 = R_8$ |
|---|---|---|---|---|
| V | D | H | $CH_3$ | $CH_3$ |
| VI | D | H | $CD_3$ | $CH_3$ |
| VII | D | H | $CH_3$ | $CD_3$ |
| VIII | D | H | $CD_3$ | $CD_3$ |
| IX | D | D | $CD_3$ | $CH_3$ |

In further embodiments, a compound of the invention is selected from:

| Compound | $R_1 = R_3$ | $R_2 = R_4$ | $R_5 = R_6$ | $R_7 = R_8$ |
|---|---|---|---|---|
| X | D | H | $CH_3$ | $CH_3$ |
| XI | D | H | $CD_3$ | $CH_3$ |
| XII | D | H | $CD_3$ | $CD_3$ |

In yet some other embodiments, a compound of the invention is selected from:

| Compound | $R_1 = R_3$ | $R_2 = R_4$ | $R_5 = R_7$ | $R_6 = R_8$ |
|---|---|---|---|---|
| XIII | D | H | $CD_3$ | $CH_3$ |

In a further aspect the invention provides a compound of general formula (I), including any salts, esters, anhydrides or prodrugs thereof:

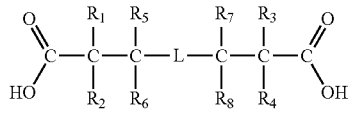

wherein

L is a straight or branched $C_8$-$C_{16}$ alkylene; optionally interrupted by at least one moiety selected from O, S, NH, $C_5$-$C_{10}$ cycloalkylene, $C_5$-$C_{10}$ cycloheteroalkylene, $C_6$-$C_{18}$ arylene, $C_6$-$C_{18}$ heteroarylene;

each of $R_1$-$R_4$ is independently $CH_3$ or $CD_3$;

each of $R_5$-$R_8$ is independently H or D;

wherein when $R_1$-$R_4$ are $CH_3$, at least one of $R_5$-$R_8$ is D; or when $R_5$-$R_8$ are H, at least one of $R_1$-$R_4$ is $CD_3$.

Thus, according to the first aspect of the application, at least one of the substituents $R_1$-$R_8$ comprises a deuterium atom. In some embodiments, at least one of $R_1$-$R_4$ is $CD_3$ and each of $R_5$-$R_8$ is independently H or D. In other embodiments, at least one of $R_5$-$R_8$ is D and each of $R_1$-$R_4$ is independently $CH_3$ or $CD_3$. In further embodiments $R_1$-$R_4$ are $CH_3$, and at least one of $R_5$-$R_8$ is D.

In some embodiments of a compound of the invention, at least one of $R_1$-$R_4$ is $CD_3$. In yet further embodiments, at least one of $R_5$-$R_8$ is D. In other embodiments, at least one of $R_1$-$R_4$ is $CD_3$ and at least one of $R_5$-$R_8$ is D.

In yet a further aspect the invention provides a compound of general formula (I), including any salts, esters, anhydrides or prodrugs thereof:

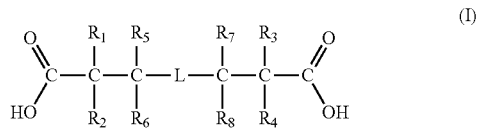

(I)

wherein

L is a straight or branched $C_8$-$C_{16}$ alkylene; optionally interrupted by at least one moiety selected from O, S, NH, $C_5$-$C_{10}$cycloalkylene, $C_5$-$C_{10}$cycloheteroalkylene, $C_6$-$C_8$ arylene, $C_6$-$C_{18}$ heteroarylene;

each of $R_1$-$R_4$ is independently $CH_3$ or $CD_3$;

each of $R_5$-$R_8$ is H;

wherein at least one of $R_1$-$R_4$ is $CD_3$.

In some embodiments, a compound of the invention is selected from:

| Compound | $R_1 = R_2 = R_3 = R_4$ | $R_5 = R_6 = R_7 = R_8$ |
|---|---|---|
| XIV | $CD_3$ | H |

In some other embodiments, a compound of the invention is selected from:

| Compound | $R_1 = R_2$ | $R_3 = R_4$ | $R_5 = R_6$ | $R_7 = R_8$ |
|---|---|---|---|---|
| XV | $CD_3$ | $CH_3$ | H | H |

In further embodiments, a compound of the invention is selected from:

| Compound | $R_1 = R_3$ | $R_2 = R_4$ | $R_5 = R_6$ | $R_7 = R_8$ |
|---|---|---|---|---|
| XVI | $CD_3$ | $CH_3$ | H | H |

In some embodiments, L is —$(CH_2)_{10}$—. In other embodiments, L is —$(CH_2)_{12}$—.

In some embodiments, compounds of the invention are selected from:

| Compound | $R_1$ | $R_2$ | $R_3$ | $R_4$ | $R_5$ | $R_6$ | $R_7$ | $R_8$ | n |
|---|---|---|---|---|---|---|---|---|---|
| 1 | D | D | D | D | $CD_3$ | $CD_3$ | $CD_3$ | $CD_3$ | 10 |
| 2 | D | D | D | D | $CH_3$ | $CH_3$ | $CH_3$ | $CH_3$ | 10 |
| 3 | H | H | H | H | $CD_3$ | $CD_3$ | $CD_3$ | $CD_3$ | 10 |
| 4 | D | D | D | D | $CD_3$ | $CD_3$ | $CD_3$ | $CD_3$ | 12 |
| 5 | D | D | D | D | $CH_3$ | $CH_3$ | $CH_3$ | $CH_3$ | 12 |
| 6 | H | H | H | H | $CD_3$ | $CD_3$ | $CD_3$ | $CD_3$ | 12 |
| 7 | $CD_3$ | $CD_3$ | $CD_3$ | $CD_3$ | H | H | H | H | 10 |
| 8 | $CD_3$ | $CD_3$ | $CD_3$ | $CD_3$ | H | H | H | H | 12 | including any salts, esters, anhydrides or prodrugs thereof.

The compounds of the present invention, as defined above, may have the ability to crystallize in more than one form, a characteristic, which is known as polymorphism, and it is understood that such polymorphic forms ("polymorphs") are within the scope of formulae (I). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

It is also noted that the compounds of the present invention may form tautomers. It is understood that all tautomers and mixtures of tautomers of the compounds of the present invention, are included within the scope of the compounds of the present invention.

The invention further provides a composition comprising a compound of the invention or any salts, esters, anhydrides or prodrugs thereof.

In some embodiments, said composition of the invention is for use as a medicament.

In a further aspect the invention provides a use of a compound of the invention or any salts, esters, anhydrides or prodrugs thereof, for the preparation of a medicament.

Pharmaceutical compositions or medicaments of the invention may additionally comprise any other suitable substances such as other therapeutically useful substances, diagnostically useful substances, pharmaceutically acceptable carriers or the like.

Pharmaceutical compositions or medicaments of the invention comprise a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions or medicaments of the invention typically include those suitable for oral, rectal, nasal, topical (including transdermal, buccal and sublingual), vaginal or parenteral (including subcutaneous, intramuscular, intravenous, intra-adipose tissue and intradermal) administration or administration via an implant. The compositions may be prepared by any method well known in the art of pharmacy. Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents.

Pharmaceutical compositions or medicaments suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition or medicament, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

In some embodiments said medicament or pharmaceutical composition of the invention is administered in a dose of 10 to 100 mg/Kg body weight per day (including doses of 10, 15, 20, 25, 30, 35, 40, 45, 50, 55, 60, 65, 70, 75, 80, 85, 90, 95 and 100 mg/Kg per day). In other embodiments, said medicament or pharmaceutical composition of the invention is administered in a dose of less than 50 mg/Kg body weight per day.

The invention also includes any salt of a compound of the invention, including any pharmaceutically acceptable salt, wherein a compound of the invention has a net charge (either positive or negative) and at least one counter ion (having a counter negative or positive charge) is added thereto to form said salt.

The term "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

In some embodiments, said medicament is for the treatment of a Metabolic Syndrome condition in a subject, including any disease, condition, symptom or disorder associated therewith.

The term "Metabolic Syndrome" (also known as metabolic syndrome X, cardiometabolic syndrome, syndrome X, insulin resistance syndrome, Reaven's syndrome, and CHAOS) is meant to encompass is a condition of a subject defined by the combination of conditions/disorders/symptoms that, when occurring together, increase the risk of developing cardiovascular disease and/or diabetes.

A subject suffering from Metabolic Syndrome condition is diagnosed with at least three of the below symptoms (Alberti et al, *Circulation* 2009; 120: 1640-1645):
  elevated waist circumference (population- and country-specific; US: Men>102 cm, Women>88 cm);
  elevated triglycerides level in the blood (≥150 mg/dL) or drug treatment for elevated triglycerides;
  reduced HDL cholesterol levels in the blood (<40 mg/dl for males and <50 mg/dL for females) or drug treatment for reduced HDL-cholesterol;
  elevated blood pressure (systolic ≥130 mmHg and/or diastolic ≥85 mmHg) or drug treatment for elevated blood pressure;
  elevated fasting glucose levels in the blood (≥100 mg/dL) or drug treatment for elevated glucose.

Furthermore, it is noted that high-sensitivity C-reactive protein (hs-CRP) is used as a marker to predict coronary vascular diseases in Metabolic Syndrome.

Cconditions/disorders/symptoms associated with Metabolic Syndrome is any one of dyslipidemia, hypertriglyceridemia, diabetes (including type 2 diabetes mellitus (T2DM) and non-insulin dependent diabetes (NIDD) and any symptoms associated therewith), obesity, cancer, hypertension and neurodegeneration.

The symptom associated with T2DM is any one of insulin resistance, hyperglycemia, diabetic dyslipidemia, diabetes macrovascular disease and diabetes microvascular disease. In some, the said condition may be prediabetes.

Where dyslipidemia is concerned, the present invention may be intended for any or all of the following: elevating the plasma level of HDL-cholesterol, for example by at least 5%, at least 10%, at least 15%, at least 20%, at least 25%, or even at least 30% or 35% as compared to the level prior to treatment; additionally, the plasma level of HDL-cholesterol may be elevated above at least 30 or 40 mg/DL; further, the invention may comprise maintaining the plasma level of HDL-cholesterol above the level prior to the treatment by the percentages described above and/or above 30 or 40 mg/DL; decreasing the plasma level of LDL-cholesterol for example by at least 5%, at least 10%, at least 15%, at least 20%, at least 25%, at least 30%, at least 40%, at least 50% or even at least 55 or 60% as compared to the level prior to treatment; additionally, the plasma level of LDL-cholesterol may be decreased below at least 190 mg/DL, at least 160 mg/DL, at least 130 mg/DL or even at least 100 mg/DL; further, the invention may comprise maintaining the plasma level of LDL-cholesterol below the level prior to the treatment by the percentages described above and or below the values described above; decreasing the plasma level of VLDL-cholesterol, for example by at least 5%, at least 10%, at least 20%>, at least 25%>, or even at least 30% or 35%> as compared to the level prior to treatment; further, the invention may comprise maintaining the plasma level of VLDL-cholesterol below the level prior to the treatment by these percentages; decreasing the plasma level of cholesterol, for example by at least 10%), at least 15%, at least 20%, at least 25%, at least 30%, at least 40%, at least 50% or even at least 55 or 60% as compared to the level prior to treatment; additionally, the plasma level of total cholesterol may be decreased below at least 240 mg/DL or at least 200 mg/DL; further, the invention may comprise maintaining the plasma level of total cholesterol below the level prior to the treatment by the percentages described above and/or below the values described above; decreasing the plasma level of triglycerides, for example by at least 7%, at least 10%, at least 15%, at least 20%, at least 25%, at least 30%, at least 40%, at least 50% or even at least 55 or 60% as compared to the level prior to treatment, additionally, the plasma level of triglycerides may be decreased below at least 200 mg/DL or at least 150 mg/DL; further, the invention may comprise maintaining the plasma level of cholesterol below the level prior to the treatment by the percentages described above and/or below the values described above.

An additional aspect of the present invention concerns the use of a composition of the invention for delaying the onset of non-insulin dependent diabetes mellitus in a human subject susceptible thereto.

In some of these embodiments said disease, condition or disorder associated with Metabolic Syndrome is selected from dyslipidemia, diabetes, obesity, cancer, hypertension, neurodegeneration.

In a further aspect the invention provides a compound as defined hereinabove, or any salts, esters, anhydrides or prodrugs thereof, for use in the treatment of a disease, condition, symptom or disorder associated with Metabolic Syndrome.

In another one of its aspects the invention provides a method of treating a disease, condition, symptom or disorder associated with Metabolic Syndrome in a subject, said method comprising administering to said subject an effective amount of at least one compound as defined hereinabove.

In some embodiments, said medicament is for the treatment of diabetes (including type I and II) in a subject, including a disease, condition, symptom or disorder associated therewith.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
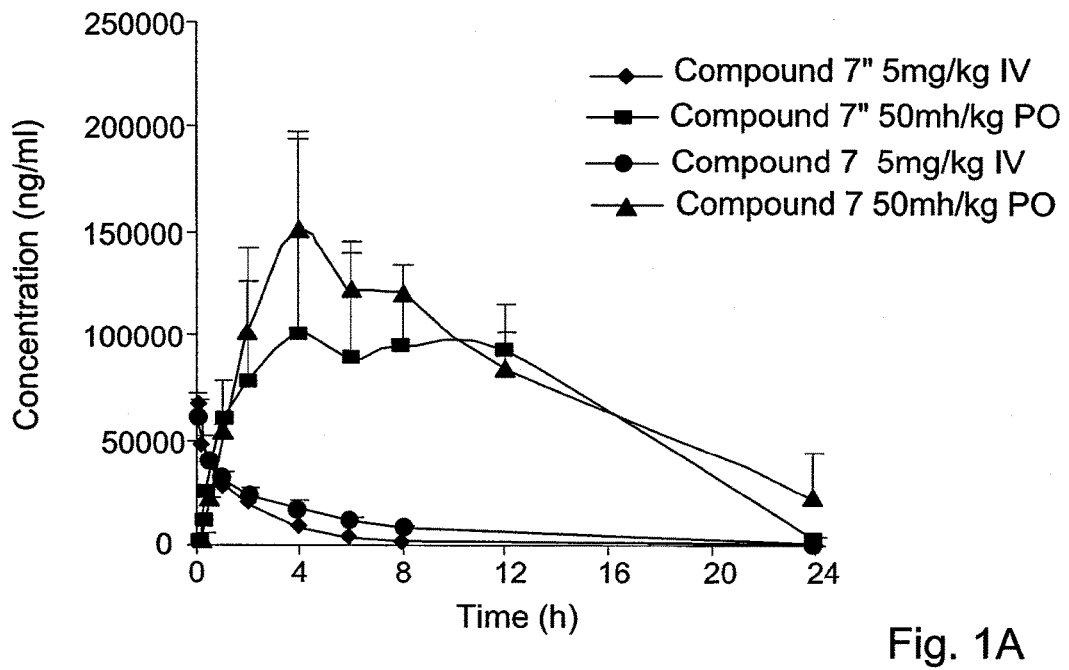
FIGS. 1A-1B show the mean plasma levels curves (with S.D.) of compounds 7", 1", 7 and 1 (administered 5 mg/kg body weight iv or 50 mg/kg body weight po).

Example 1: Process for the preparation of 1,1,16,16-Tetra(ethoxycarbonyl)-2,2,15,15-tetramethyl-hexadecane

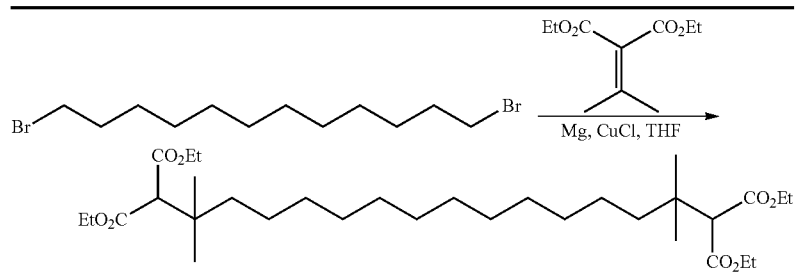

| Reagent | Amount | Mol. Wt. | Mmol | Lot number |
|---|---|---|---|---|
| 1,12-Dibromododecane | 14.0 g | 328.13 | 42.7 | Aldrich S41671 |
| Magnesium, small turnings | 2.19 g | 24.31 | 90.0 | Aldrich 15621KH |
| Tetrahydrofuran | 110 mL | | | Aldrich 22796MMV |
| Diethyl isopropylidenemalonate | 18.0 g | 200.23 | 89.9 | Fluka 1191218 |
| Copper(I) chloride | 0.150 g | 90.00 | 1.51 | Aldrich MKAA0267 |
| 3N Hydrochloric acid | 80 mL | | | Made from Fisher 092605 |
| Heptane | As needed | | | BDH090409D |
| Methyl tert-butyl ether | As needed | | | Aldrich 66396JK |
| Silica gel | As needed | | | EMD TA1366285 |

A 500 mL 3 neck round bottom flask was charged with magnesium turnings (2.19 g). The flask was flushed with nitrogen and anhydrous tetrahydrofuran (100 mL) was added. A solution of 1,12-dibromododecane (14.0 g) in tetrahydrofuran (10 mL) was added dropwise to the magnesium suspension over 20 min. The reaction mixture became warm during the addition. The reaction was stirred at room temperature for 4 h after the addition was complete. The mixture was cooled in an ice bath and copper(I) chloride (0.150 g) was added. Diethyl isopropylidenemalonate (18.0 g) was added dropwise from a syringe over 15 min. The cooling bath was removed and the reaction was allowed to warm to room temperature and stir overnight. The reaction was quenched with 3 N hydrochloric acid (80 mL). Heptane (100 mL) was added and the layers were separated. The aqueous layer was extracted with methyl tertbutyl ether (100 mL). The combined organic extracts were filtered through a plug of silica gel (60 mL fritted funnel filled ⅔ full with silica gel). The silica gel was further washed with 1:1 heptane-methyl tert-butyl ether (100 mL). The filtrate was concentrated under reduced pressure to give a light amber oil. The crude product was distilled using a Kugelrohr apparatus under vacuum (5 mm Hg) with an oven temperature of 180° C. A small amount of colorless liquid distilled which was predominately unreacted diethyl isopropylidenemalonate. The residue was allowed to cool to room temperature and was weighed to give 1,1,16,16-tetra(ethoxycarbonyl)-2,2,15,15-tetramethylhexadecane (19.6 g, 80.3%).

Example 2: Process for the Preparation of Diethyl 3,3,16,16-tetramethyl-1,18-octadecanedioate cooled to room temperature and was poured into DI water (320 mL) containing concentrated hydrochloric acid (3 mL). The mixture was extracted with 3:1 heptane-methyl tert-butyl ether (400 mL). The organic layer was washed with DI water (3×150 mL). The organic layer was concentrated under reduced pressure to give a brown liquid. The crude product was purified on a Single Step silica gel cartridge (160 g) using 4:1 heptane-dichloromethane as eluent followed by 1:1 heptane-dichloromethane. Fractions that eluted off the column with 1:1 heptane-dichloromethane were combined and concentrated under reduced pressure to give

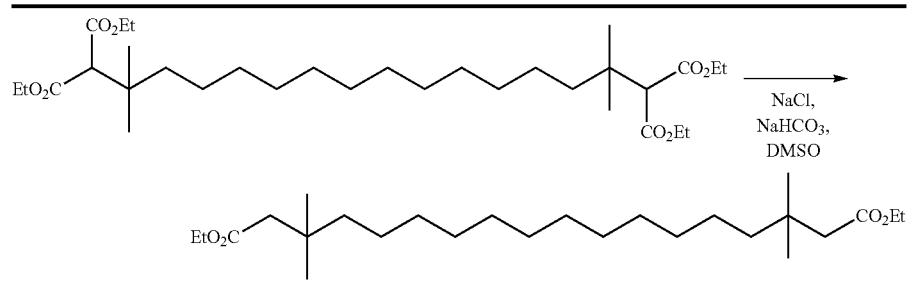

| Regent | Amount | Mol. Wt. | Mmol | Lot number |
|---|---|---|---|---|
| 1,1,16,16-Tetra(ethoxycarbonyl)-2,2,15,15-tetramethylhexadecane | 10.0 g | 570.80 | 17.5 | Aptuit 10-163-04-12 |
| Sodium chloride | 2.57 g | 58.44 | 44.0 | BDH 67573 |
| Sodium bicarbonate | 2.21 g | 84.01 | 26.3 | Mallinckrodt E23615 |
| Dimethyl sulfoxide | 80 mL | | | Aldrich 26696MJ |
| DI water | As needed | | | |
| Concentrated hydrochloric acid | 3 mL | | | Fisher 092605 |
| Heptane | As needed | | | BDH090409D |
| Methyl tert-butyl ether | As needed | | | Aldrich 66396JK |
| Single Step silica gel cartridge, 160 g | 1 | | | Thomson TIC345739306211 OA |
| Dichloromethane | As needed | | | Burdick & Jackson DB763 |

A 250 mL round bottom flask was charged with 1,1,16,16-tetra(ethoxycarbonyl)-2,2,15,15-tetramethylhexadecane (10.0 g), sodium chloride (2.57 g), sodium bicarbonate (2.21 g) and dimethyl sulfoxide (80 mL). The mixture was heated in a 180° C. oil bath for 24 h. The reaction mixture was diethyl 3,3,16,16-tetramethyl-1,18-octadecanedioate (4.50 g, 60.2%) as a light yellow liquid.

Example 3: Process for the Preparation of 33,16,16-Tetramethyl-1,18-[2-D2,17-D2]octadecanedioic acid (Compound 5)

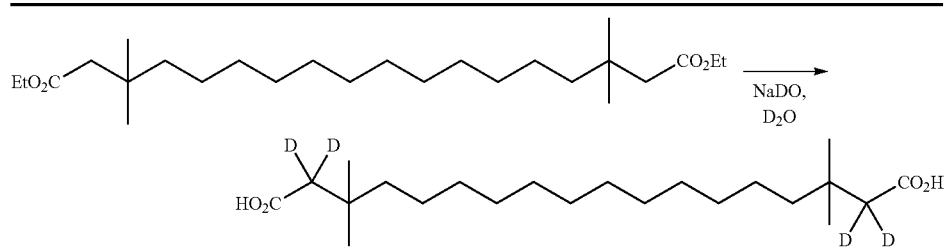

| Regent | Amount | Mol. Wt. | Mmol | Lot number |
|---|---|---|---|---|
| Diethyl 3,3,16,16-tetramethyl-1,18-octadecanedioate | 4.46 g | 426.67 | 10.5 | Aptuit 10-163-05-33 |
| Sodium deuteroxide (40% in deuterium oxide) | 10 mL | | | Aldrich MKAA3249 |
| Deuterium oxide | 10 mL | | | Aldrich MKBF3761V |
| Concentrated hydrochloric acid | As needed | | | Fisher 092605 |
| Methyl tert-butyl ether | As needed | | | Aldrich 66396JK |
| Isopropyl alcohol | As needed | | | EMD 48121 |
| Ethanol | As needed | | | EMD 201004807 |
| Trifluoroacetic acid | 2 mL | | | Aldrich 01113$^{TH}$ |
| DI water | As needed | | | |

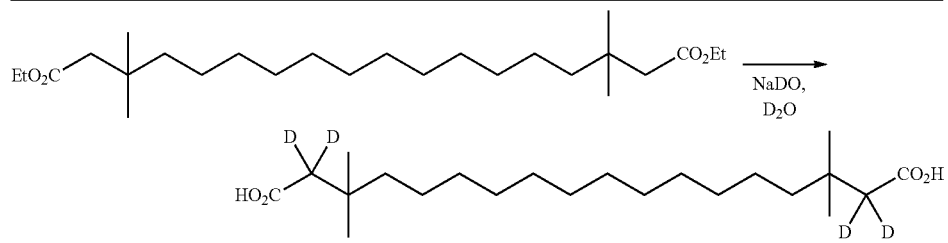

| Regent | Amount | Mol. Wt. | Mmol | Lot number |
|---|---|---|---|---|
| Dichloromethane | As needed | | | Burdick & Jackson DC419 |
| Heptane | As needed | | | BDH090409D |
| Methanol | As needed | | | BDH022310B |
| Celite 545 | 7.0 g | | | EMD 49085 |

A 150 ml 316 stainless steel bomb was charged with diethyl 3,3,16,16-tetramethyl-1,18-octadecanedioate (4.46 g), sodium deuteroxide (10 mL, 40% in deuterium oxide) and deuterium oxide (10 mL). The bomb was sealed and was heated in a 200° C. oil bath for 40 h. The bomb was cooled to room temperature and was opened. The liquid contents of the bomb were poured out and acidified with concentrated hydrochloric acid. The aqueous mixture was extracted with methyl tert-butyl ether (100 mL). Isopropyl alcohol (100 mL) was added to the bomb. A spatula was used to scrape the inside of the bomb to remove the soapy solid. The contents of the bomb were poured out as an amber solution and some solid. Ethanol (100 mL) was added to the bomb. The bomb was again scraped and emptied. The ethanol and isopropyl alcohol washes were combined and trifluoroacetic acid (2 mL) was added. The mixture was stirred until the solid dissolved. The resulting solution was concentrated under reduced pressure to give an oily residue. Methyl tert-butyl ether (150 mL) and DI water (100 mL) were added. The mixture was vigorously stirred, and then the layers were separated. The methyl tert-butyl ether layer was combined with the previous methyl tert-butyl ether extract. The solvent was removed under reduced pressure to give an off white solid. The solid was slurried in dichloromethane (10 mL) and heptane (30 mL). The solid was filtered, washed with heptane (2×10 mL) and dried under reduced pressure to give a cream colored solid. The solid was placed in a 1 L Erlenmeyer flask and methanol (500 mL) was added. The mixture was stirred at room temperature for 10 min to give a cloudy solution. The mixture was filtered through Celite 545 (7.0 g) and the solid was washed with methanol (2×100 ml). The filtrate was concentrated under reduced pressure to give an off white solid. The solid was slurried in dichloromethane (10 mL) and heptane (30 mL). The solid was filtered, washed with heptane (10 mL) and dried under high vacuum to give 3,3,16,16-tetramethyl-1,18-[2-D2,17-D2]octadecanedioic acid (3.2684 g, 83.1%) as a white solid.

Example 4: Process for the Preparation of 1,1,14,14-Tetra(ethoxycarbonyl)-2,2,13,13-tetramethyltetradecane

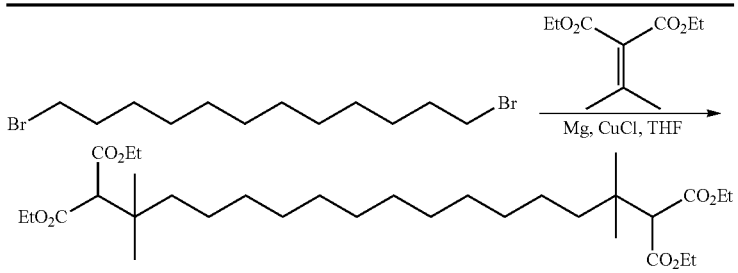

| Regent | Amount | Mol. Wt. | Mmol | Lot number |
|---|---|---|---|---|
| 1,10-Dibromodecane | 12.21 g | 300.07 | 40.7 | Aldrich 70246DJ |
| Magnesium, small turnings | 2.19 g | 24.31 | 90.0 | Aldrich 15621KH |
| Tetrahydrofuran | 110 mL | | | Aldrich 22796MMV |
| Diethyl isopropylidenemalonate | 18.0 g | 200.23 | 89.9 | Fluka 1191218 |
| Copper(I) chloride | 0.150 g | 99.00 | 1.51 | Aldrich MKAA0267 |
| 3N Hydrochloric acid | 80 mL | | | Made from Fisher 092605 |
| Heptane | As needed | | | BDH090409D |
| Methyl tert-butyl ether | As needed | | | Aldrich 66396JK |
| Silica gel | As needed | | | EMD TA1366285 |

A 500 mL 3 neck round bottom flask was charged with magnesium turnings (2.19 g). The flask was flushed with nitrogen and anhydrous tetrahydrofuran (100 mL) was added. A solution of 1,12-dibromododecane (14.0 g) in tetrahydrofuran (10 mL) was added dropwise to the magnesium suspension over 20 min. The reaction mixture got warm during the addition. The reaction was stirred at room temperature for 4 h after the addition was complete. The mixture was cooled in an ice bath and copper(I) chloride (0.150 g) was added. Diethyl isopropylidenemalonate (18.0 g) was added dropwise from a syringe over 15 min. The cooling bath was removed and the reaction was allowed to warm to room temperature and stir overnight. The reaction was quenched with 3 N hydrochloric acid (80 mL). Heptane (100 mL) was added and the layers were separated. The aqueous layer was extracted with methyl tertbutyl ether (100 mL). The combined organic extracts were filtered through a plug of silica gel (60 mL fritted funnel filled ⅔ full with silica gel). The silica gel was further washed with 1:1 heptane-methyl tert-butyl ether (100 mL). The filtrate was concentrated under reduced pressure to give a light amber oil. The crude product was distilled using a Kugelrohr apparatus under vacuum (5 mm Hg) with an oven temperature of 180° C. A small amount of colorless liquid distilled which was predominately unreacted diethyl isopropylidenemalonate. The residue was allowed to cool to room temperature and was weighed to give 1,1,14,14-tetra(ethoxycarbonyl)-2,2,13,13-tetramethyltetradecane (15.9 g, 72.1%).

Example 5: Process for the Preparation of Diethyl 3,3,14,14-tetramethyl-1,16-hexadecanedioate

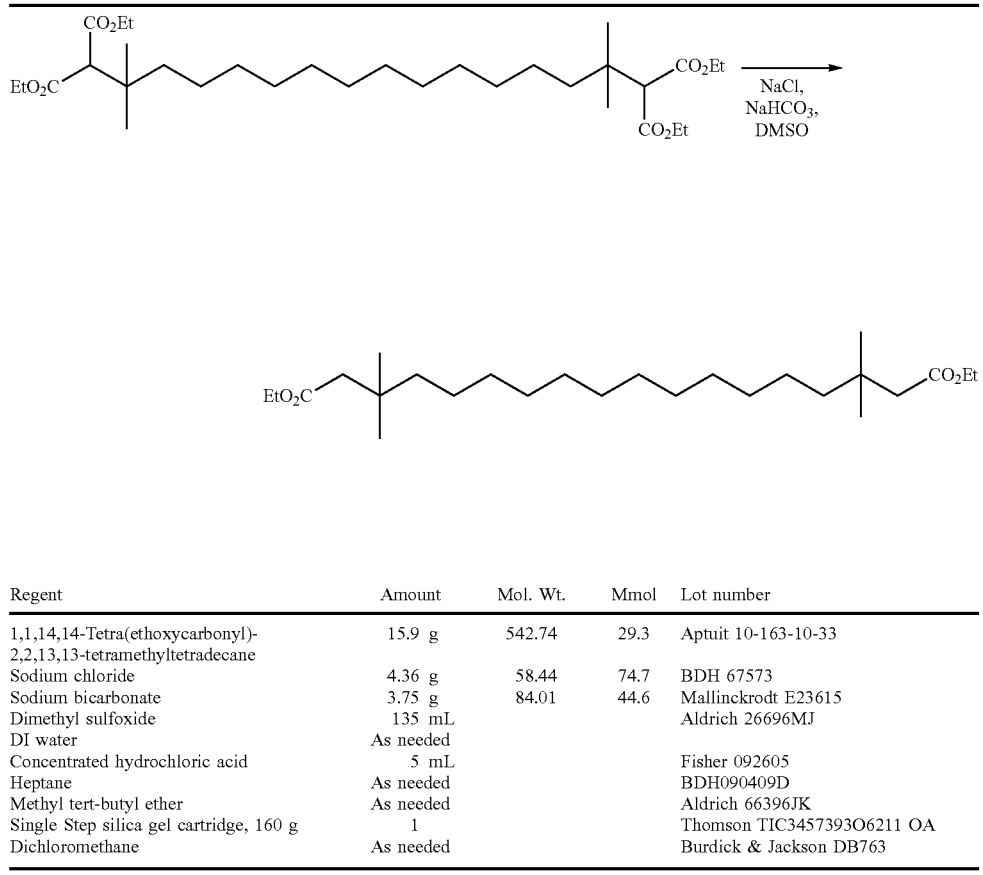

| Regent | Amount | Mol. Wt. | Mmol | Lot number |
|---|---|---|---|---|
| 1,1,14,14-Tetra(ethoxycarbonyl)-2,2,13,13-tetramethyltetradecane | 15.9 g | 542.74 | 29.3 | Aptuit 10-163-10-33 |
| Sodium chloride | 4.36 g | 58.44 | 74.7 | BDH 67573 |
| Sodium bicarbonate | 3.75 g | 84.01 | 44.6 | Mallinckrodt E23615 |
| Dimethyl sulfoxide | 135 mL | | | Aldrich 26696MJ |
| DI water | As needed | | | |
| Concentrated hydrochloric acid | 5 mL | | | Fisher 092605 |
| Heptane | As needed | | | BDH090409D |
| Methyl tert-butyl ether | As needed | | | Aldrich 66396JK |
| Single Step silica gel cartridge, 160 g | 1 | | | Thomson TIC345739306211 OA |
| Dichloromethane | As needed | | | Burdick & Jackson DB763 |

A 250 mL round bottom flask was charged with 1,1,14,14-terra(ethoxycarbonyl)-2,2,13,13-tetramethyltetradecane (15.9 g), sodium chloride (4.36 g), sodium bicarbonate (3.75 g) and dimethyl sulfoxide (135 mL). The mixture was heated in a 180° C. oil bath for 42 h. The reaction mixture was cooled to room temperature and was poured into DI water (500 mL) containing concentrated hydrochloric acid (5 mL). The mixture was extracted with 3:1 heptane-methyl tert-butyl ether (400 mL). The organic layer was washed with DI water (3×150 mL). The organic layer was concentrated under reduced pressure to give a brown liquid. The crude product was purified on a Single Step silica gel cartridge (160 g) using 3:2 heptane-dichloromethane as eluent. Fractions that contained product were combined and concentrated under reduced pressure to give diethyl 3,3,14,14-tetramethyl-1,16-hexadecanedioate (4.00 g, 34.2%) as a light yellow liquid.

Example 6: Process for the Preparation of 3,3,14,14-Tetramethyl-1,16-[2-D2,15-D2]hexadecanediol acid (Compound 2)

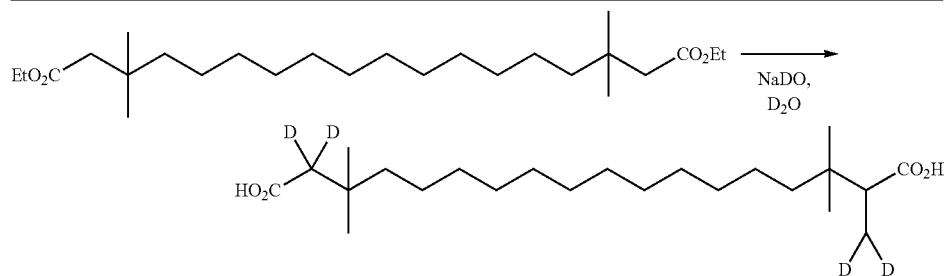

| Regent | Amount | Mol. Wt. | Mmol | Lot number |
|---|---|---|---|---|
| Diethyl 3,3,14,14-tetramethyl-1,16-tetradecanedioate | 4.00 g | 396.62 | 10.0 | Aptuit 10-163-01-32 |
| Sodium deuteroxide (40% in deuterium oxide) | 12 mL | | | Aldrich MKAA3249 |
| Deuterium oxide | 12 mL | | | Aldrich MKBF3761V |
| Methyl tert-butyl ether | As needed | | | Aldrich 66396JK |
| Ethanol | As needed | | | EMD 201004807 |
| Trifluoroacetic acid | 4 mL | | | Aldrich 01113$^{TH}$ |
| DI water | As needed | | | |
| Dichloromethane | As needed | | | Burdick & Jackson DC419 |
| Heptane | As needed | | | BDH090409D |
| Methanol | As needed | | | BDH022310B |
| Celite 545 | 5.0 g | | | EMD 49085 |

A 150 ml 316 stainless steel bomb was charged with diethyl 3,3,14,14-tetramethyl-1,16-tetradecanedioic acid (4.00 g), sodium deuteroxide (12 mL, 40% in deuterium oxide) and deuterium oxide (12 mL). The bomb was sealed and was heated in a 200° C. oil bath for 48 h. The bomb was cooled to room temperature and then opened. The soapy solid was broken up with a spatula so the aqueous contents of the bomb could be poured out. Four 50 mL portions of ethanol were used to wash the waxy solids out of the bomb. The ethanol washes were combined and trifluoroacetic acid (4 mL) was added. The mixture was stirred for 30 min until the solid dissolved. The resulting solution was concentrated under reduced pressure to give an oily residue. Methyl tert-butyl ether (150 mL) and DI water (100 mL) were added. The mixture was vigorously stirred, and then the layers were separated. The methyl tert-butyl ether layer was concentrated under reduced pressure to give a white solid. The solid was slurried in dichloromethane (10 mL) and heptane (20 mL). The solid was filtered, washed with heptane (10 mL) and dried under reduced pressure to give a white solid. The filtrate was concentrated under reduced pressure to give a solid. Both solids were placed in a 1 L Erlenmeyer flask and methanol (300 mL) was added. The mixture was stirred at room temperature for 10 min to give a slightly cloudy solution. The mixture was filtered through Celite 545 (5.0 g) and the solid was washed with methanol (100 ml). The filtrate was concentrated under reduced pressure to give an off white solid. The solid was slurried in dichloromethane (10 mL) and heptane (30 mL). The solid was filtered, washed with heptane (10 mL) and dried under high vacuum to give 3,3,14,14-tetramethyl-1,16-[2-D2,15-D2]tetradecanedioic acid (2.3371 g, 67.4%) as a white solid.

Example 7: Process for the Preparation of 1,1,16,16,-Tetra(ethoxycarbonyl)2,2,15,15,-[D12]tetramethylhexadecane

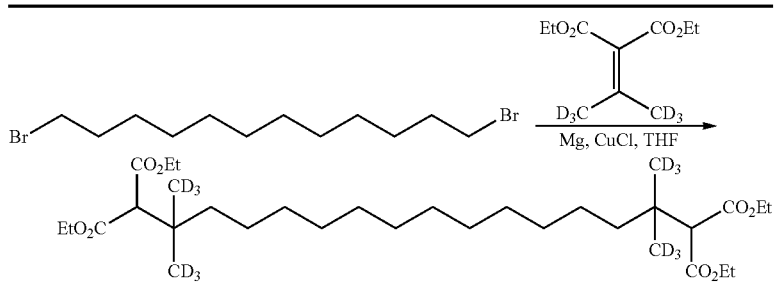

| Regent | Amount | Mol. Wt. | Mmol | Lot number |
|---|---|---|---|---|
| 1,12-Dibromododecane | 5.32 g | 328.13 | 16.2 | Aldrich S41671 |
| Magnesium, small turnings | 0.88 g | 24.31 | 36.0 | Aldrich 15621KH |
| Tetrahydrofuran | 45 mL | | | Aldrich 22796MMV |
| Diethyl [D$_6$]isopropylidenemalonate | 7.00 g | 206.27 | 33.9 | Aptuit 10-163-02-04 |
| Copper(I) chloride | 75 mg | 99.00 | 0.76 | Aldrich MKAA0267 |
| 3N Hydrochloric acid | 40 mL | | | Made from Fisher 092605 |

-continued

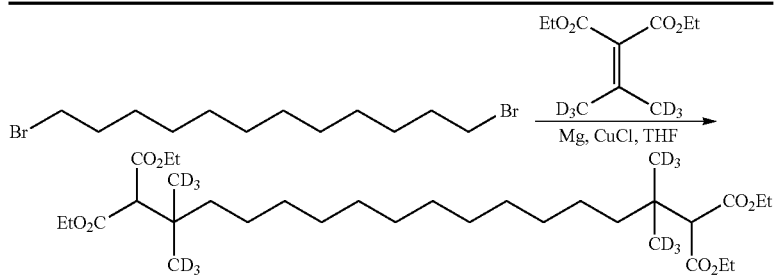

| Regent | Amount | Mol. Wt. | Mmol | Lot number |
|---|---|---|---|---|
| Heptane | As needed | | | BDH090409D |
| Methyl tert-butyl ether | As needed | | | Aldrich 66396JK |
| Silica gel | As needed | | | EMD TA1366285 |

A 250 mL round bottom flask was charged with magnesium turnings (0.88 g). The flask was flushed with nitrogen and anhydrous tetrahydrofuran (40 mL) was added. A solution of 1,12-dibromododecane (5.32 g) in tetrahydrofuran (5 mL) was added dropwise to the magnesium suspension over 15 min. The reaction mixture became warm during the addition. The reaction was stirred at room temperature for 4 h after the addition was complete. The mixture was cooled in an ice bath and copper(I) chloride (0.150 g) was added. Diethyl [D6]isopropylidenemalonate (7.0 g) was added dropwise from a syringe over 5 min. The cooling bath was removed and the reaction was allowed to warm to room temperature and to stir overnight. The reaction was quenched with 3 N hydrochloric acid (40 mL). Heptane (50 mL) was added and the layers were separated. The aqueous layer was extracted with methyl tert-butyl ether (50 mL). The combined organic extracts were filtered through a plug of silica gel (60 mL fritted funnel filled half full with silica gel). The silica gel was further washed with methyl tert-butyl ether (100 mL). The filtrate was concentrated under reduced pressure to give a golden oil. The crude product was distilled using a Kugelrohr apparatus under vacuum (5 mm Hg) with an oven temperature of 180° C. A small amount of colorless liquid distilled which was predominately unreacted diethyl isopropylidenemalonate. The residue was allowed to cool to room temperature and was weighed to give 1,1,16,16-tetra(ethoxycarbonyl)-2,2,15,15-[D12]tetramethylhexadecane (8.2 g, 87%).

Example 8: Process for the Preparation of Diethyl 3,3,14,14-[D12]tetramethyl-1,18-

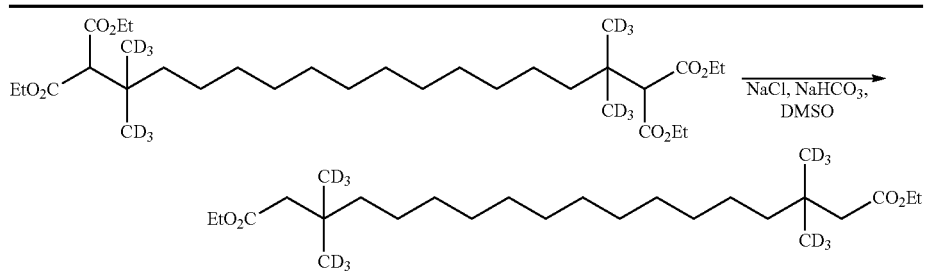

| Regent | Amount | Mol. Wt. | Mmol | Lot number |
|---|---|---|---|---|
| 1,1,16,16-Tetra(ethoxycarbonyl)-2,2,15,15-[$D^{12}$]tetramethylhexadecane | 8.2 g | 582.87 | 14.1 | Aptuit 10-163-06-34 |
| Sodium chloride | 2.07 g | 58.44 | 35.2 | BDH 67573 |
| Sodium bicarbonate | 1.77 g | 84.01 | 21.0 | Mallinckrodt E23615 |
| Dimethyl sulfoxide | 65 mL | | | Aldrich 26696MJ |
| DI water | As needed | | | |
| Concentrated hydrochloric acid | 3 mL | | | Fisher 092605 |
| Heptane | As needed | | | BDH090409D |
| Methyl tert-butyl ether | As needed | | | Aldrich 66396JK |
| Single Step silica gel cartridge, 160 g | 1 | | | Thomson TIC345739306211 OA |
| Dichloromethane | As needed | | | Burdick & Jackson DB763 |

A 250 mL round bottom flask was charged with 1,1,16,16-tetra(ethoxycarbonyl)-2,2,15,15-[D12]tetramethylhexadecane (8.2 g), sodium chloride (2.07 g), sodium bicarbonate (1.77 g) and dimethyl sulfoxide (65 mL). The mixture was heated in a 180° C. oil bath for 50 h. The reaction mixture was cooled to room temperature and was poured into DI water (250 mL) containing concentrated hydrochloric acid (3 mL). The mixture was extracted with 2:1 heptane-methyl tert-butyl ether (300 mL). The organic layer was washed with DI water (3×150 mL). The organic layer was concentrated under reduced pressure to give a brown liquid. The crude product was purified on a Single Step silica gel cartridge (160 g) using 3:2 heptane-dichloromethane as eluent. Fractions that contained product were combined and concentrated under reduced pressure to give diethyl 3,3,16,16-[D12]tetramethyl-1,18-octadecanedioate (3.10 g, 50.2%) as an orange liquid.

Example 9: Process for the Preparation of 3,3,16,16-[D12]Tetramethyl-1,18-octadecanedioic acid (Compound 6)

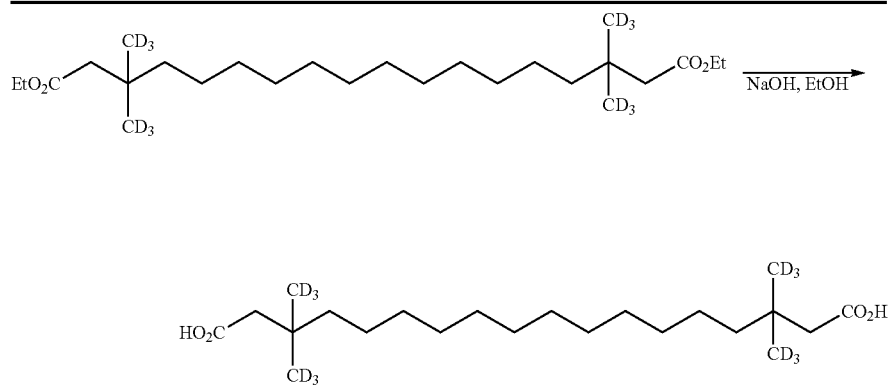

| Regent | Amount | Mol. Wt. | Mmol | Lot number |
|---|---|---|---|---|
| Diethyl 3,3,16,16-[D$_{12}$]tetramethyl-1,18-tetradecanedioate | 3.10 g | 438.75 | 7.07 | Aptuit 10-163-07-28 |
| Sodium hydroxide | 1.75 g | 40.0 | 43.8 | Fisher 081317 |
| Ethanol | 70 mL | | | EMD 201004807 |
| DI water | 200 mL | | | |
| Concentrated hydrochloric acid | 10 mL | | | Fisher 092605 |
| Methyl tert-butyl ether | As needed | | | Aldrich 66396JK |
| Dichloromethane | As needed | | | Burdick & Jackson DC419 |
| Heptane | As needed | | | BDH090409D |
| Methanol | As needed | | | BDH022310B |
| Silica gel | As needed | | | EMD TA1366285 |
| Celite 545 | 4.8 g | | | EMD 49085 |

A 250 mL round bottom flask was charged with diethyl 3,3,16,16-[D12]dimethyl-1,18-octadecanedioate (3.10 g), sodium hydroxide (1.75 g) and ethanol (70 mL). The mixture was heated in a 80° C. oil bath overnight. The reaction was allowed to cool to room temperature. Most of the ethanol was removed under reduced pressure. DI water (100 mL) was added and the mixture was acidified with concentrated hydrochloric acid (10 mL). The solid that formed was filtered and washed with DI water (100 mL). The solid was dissolved in 3% methanol in dichloromethane (100 mL). The solution was passed through a plug of silica gel (60 mL fritted funnel filled ⅔ full). The silica gel was further eluted with 3% methanol in dichloromethane (300 mL). The filtrate was concentrated under reduced pressure to give a yellow solid. The solid was suspended in methyl tert-butyl ether (5 mL) and heptane (25 mL). The solid was filtered, washed with heptane (2×5 mL) and dried under reduced pressure. The solid was placed in a 500 mL Erlenmeyer flask and methanol (250 mL) was added. The mixture was stirred for 10 min at room temperature giving a cloudy solution. The solution was filtered through a pad of Celite 545 (4.8 g), and the Celite was further washed with methanol (100 mL). The filtrate was concentrated under reduced pressure to give an off white solid. The solid was suspended in dichloromethane (5 mL) and heptane (15 mL). The solid was filtered, washed with heptane (10 mL) and dried under high vacuum to give 3,3,16,16-[D12]tetramethyl-1,18-octadecanedioic acid (1.5740 g, 58.2%) as a white solid.

Example 10: Process for the Preparation of 3,3,14,14-[D16]Tetramethyl-1,16-hexadecanedioic acid (Compound 1) and 3,3,14,14-[D12]Tetramethyl-1,16-hexadecanedioic acid (Compound 3)

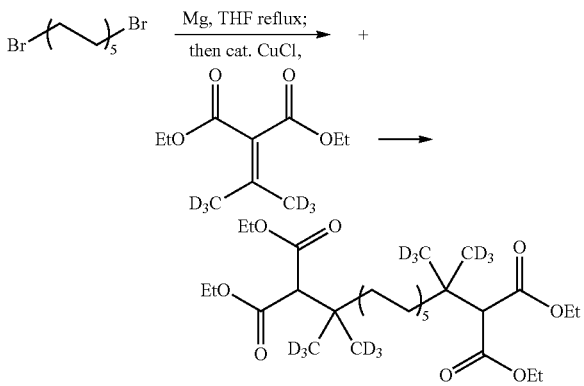

A 1 L, 3-neck, round bottom flask equipped with a magnetic stir bar, reflux condenser, addition funnel, and thermometer was flushed with nitrogen for 30 min. Into the flask was charged magnesium turnings (5.82 g, 239 mmoles), anhydrous THF (208 mL), and a single iodine crystal to initiate the reaction. A solution of 1,10-dibromodecane (34.2 g, 114 mmoles) in anhydrous THF (90 mL) was prepared. A portion of this solution (~5 mL) was added to the reaction. The mixture was heated to a mild reflux (65° C.) using a temperature-controlled oil bath and was held at reflux until the yellow color of 12 had disappeared (~30 min). The remaining solution was added dropwise over ~30 min, maintaining a gentle reflux. The reaction was refluxed for an additional 2 h. The reaction was cooled to −2° C. (ice/water/CO$_2$ bath), CuCl(s) (0.79 g, 8.0 mmoles) was added in a single portion, and the mixture was stirred for additional 10 min. A solution of diethyl isopropylidenemalonate (dimethyl-D6) (47.0 g, 228 mmoles) in anhydrous THF (50 mL) was added to the reaction dropwise at a rate to keep the temperature ≤5° C. After addition was completed, the reaction mixture was allowed to warm to ambient temperature and stirred overnight. The reaction was cooled to 0° C., and then a solution of 12N HCl(aq) (174 mL) in water (261 mL) was added in a slow stream maintaining the internal temperature below 20° C. The mixture was extracted with Et$_2$O (1×250 mL; 3×100 mL), and the combined Et$_2$O extracts were washed with sat. NaHCO$_3$(aq) (3×150 mL) and sat. NaCl(aq) (1×150 mL). The Et$_2$O layer was dried with MgSO$_4$, filtered, and concentrated in vacuo to a crude oil (62.7 g) which was purified by flash chromatography (silica gel, EtOAc/hexanes gradient) to afford compound 1 and compound 3 precursor tetraester (D12) (35.2 g, 56% yield) as a colorless oil.

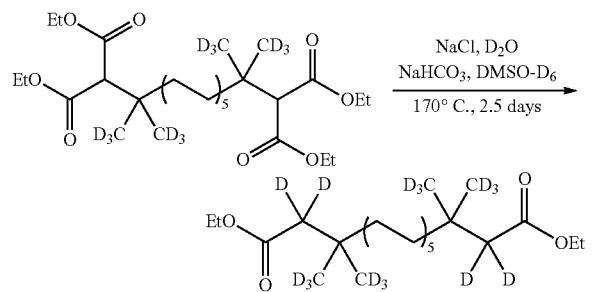

Compound 1 precursor tetraester (D12) (34.0 g, 61.3 mmoles), DMSO-D6 (268 mL), D$_2$O (9.2 mL, 457 mmoles), NaCl(s) (8.9 g, 152 mmoles), and NaHCO$_3$(s) (7.7 g, 91.7 mmoles) were charged into a 500-mL round bottom flask equipped with a magnetic stir bar, reflux condenser (with no coolant flow) and an internal thermometer. A temperature-controlled oil bath was used for heating. With stirring, the flask was heated in the oil bath set to 177° C. The reaction was heated for 48 hours until complete by TLC. TLC control: ten drops of the reaction was shaken with 30 drops (0.6 mL) of 0.1M HCl(aq) and 0.5 mL of Et$_2$O. TLC of the Et$_2$O layer (10% EtOAc/hexanes; visualization with KMnO$_4$ stain). At intermediate stages of the reaction, a mixture of tetraester, triester (see below) and desired diester was observed.

The reaction flask was allowed to cool to room temperature and was poured into of 1M HCl(aq) (1.1 L) and extracted with Et$_2$O (4×500 mL). The Et$_2$O extracts were combined and washed with water (1×500 mL) and saturated NaCl(aq) (1×500 mL). The Et$_2$O layer was dried with MgSO$_4$, filtered, and concentrated in vacuo to an orange oil (24.6 g). The crude oil was chromatographed on silica gel using a EtOAc/hexanes gradient to obtain compound 1 Diester (D16) (18.2 g, 72% yield) as a colorless oil.

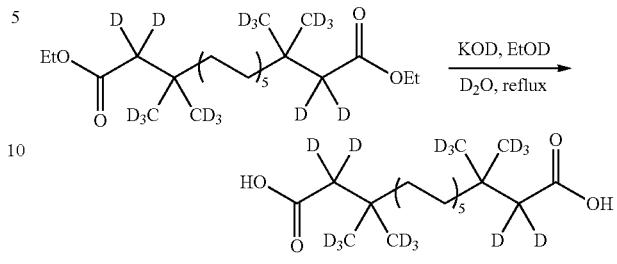

In a 1-L round bottom flask equipped with a magnetic stir bar, reflux condenser, and a nitrogen line, compound 1 diester (D16) (11.2 g, 27 mmoles) and EtOD (504 mL) were stirred to a solution. 35% KOD/D$_2$O (97 g, 596 mmoles) was added, and the solution was refluxed for 3 h. Fifteen drops of the reaction was shaken with 15 drops of 1M HCl(aq) and 0.5 mL of Et$_2$O. TLC of the Et$_2$O layer (silica gel plate; 10% EtOAc/hexanes mobile phase; visualization with KMnO$_4$ stain) showed the diester was consumed. The cooled overnight reaction was concentrated in vacuo to a thick oil which was dissolved in water (100 mL) and acidified with 12% DCl/D$_2$O (~150 mL) until the supernatant was acidic. The precipitated solid was collected by filtration and washed with a small amount of H$_2$O (2×5 mL). The solids were briefly air dried on the filter and then in vacuo at 40° C. overnight. The off-white solid was dissolved in hot ethanol-D6 (100 mL). D$_2$O (60 mL) was added slowly, and the resulting suspension was left overnight to complete crystallization. The white solid was filtered-off, washed with 50% EtOH(aq) (2×25 mL). The solids were dried in vacuo at 40° C. to constant weight for to afford compound 1 (D16) (9.0 g; 93% yield) as a white solid which passed all release testing (HPLC chemical purity, mp, GCMS IE, 1HNMR, 13CNMR, KF).

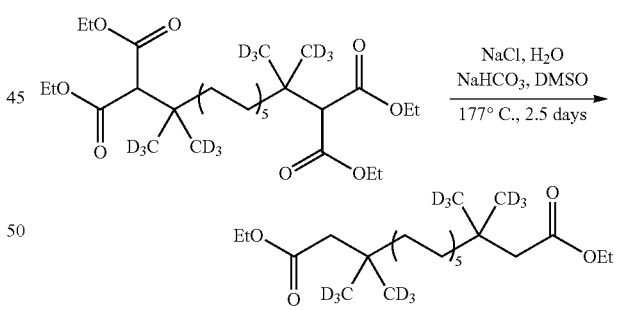

Compound 3 precursor tetraester (D12) (14.0 g, 25.2 mmoles), DMSO (110 mL), H2O (3.4 mL, 189 mmoles), NaCl(s) (3.7 g, 63.1 mmoles), and NaHCO$_3$(s) (3.2 g, 37.8 mmoles) were placed in a 250-mL round bottom flask equipped with a magnetic stir bar, reflux condenser (with no coolant flow) and an internal thermometer. A temperature-controlled oil bath was used for heating. With stirring, the flask was heated in the oil bath set to 177° C. The reaction was heated for 2.5 days until complete by TLC. The reaction mixture was poured into 440 mL of 1M HCl(aq) and extracted with Et$_2$O (4×200 mL). The Et$_2$O extracts were combined and washed with water (1×200 mL) and saturated NaCl(aq) (1×200 mL). The Et$_2$O layer was dried with MgSO₄, filtered, and concentrated in vacuo to an orange oil (10.8 g). The crude oil was chromatographed on silica gel using a EtOAc/hexanes gradient to obtain compound 3 Diester (D12) (7.8 g, 75% yield) as a colorless oil.

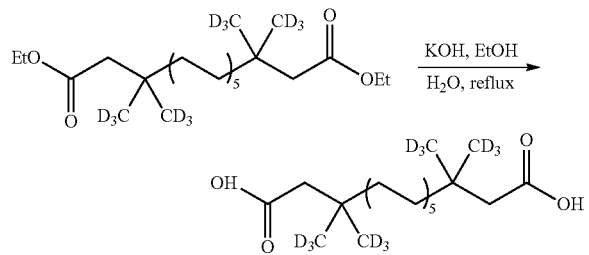

In a 1-L round bottom flask equipped with a magnetic stir bar, reflux condenser, and a nitrogen line, COMPOUND 3 diester (D12) (7.5 g, 18.3 mmoles), EtOH (337.5 mL), and water (37.5 mL) were stirred to a solution. 85% KOH (26.6 g, 402 mmoles) was added in a single portion and the resulting mixture was refluxed for 3 h. Fifteen drops of the reaction was shaken with 15 drops of 1M HCl(aq) and 0.5 mL of Et₂O. TLC of the Et₂O layer (silica gel plate; 10% EtOAc/hexanes mobile phase; visualization with KMnO4 stain) showed the diester was consumed. The cooled overnight reaction was concentrated in vacuo to an orange oil which was dissolved in water (75 mL) and acidified with 4N HCl (~110 mL). The precipitated solid was collected by filtration and washed with a small amount of H₂O (2×5 mL). The solids were briefly air dried on the filter and then in vacuo at 40° C. overnight. The off-white solid (6.9 g) was dissolved in hot ethanol (70 mL). The yellow solution was treated with charcoal (~1 g) and filtered through a pad of Celite. To the colorless solution was added water (50 mL), and the resulting slurry was left overnight to complete crystallization. The solid was collected by filtration, washed with 50% EtOH(aq) (2×25 mL) and dried in vacuo at 40° C. to constant weight to afford compound 3 (D12) (6.2 g; 95% yield) as a white solid which passed all release testing (HPLC chemical purity, mp, GCMS IE, 1HNMR, 13CNMR, KF).

Example 11: Process for the Preparation of 3,3,16,16-[D16]Tetramethyl-1,18-octadecanedioic acid (Compound 4)

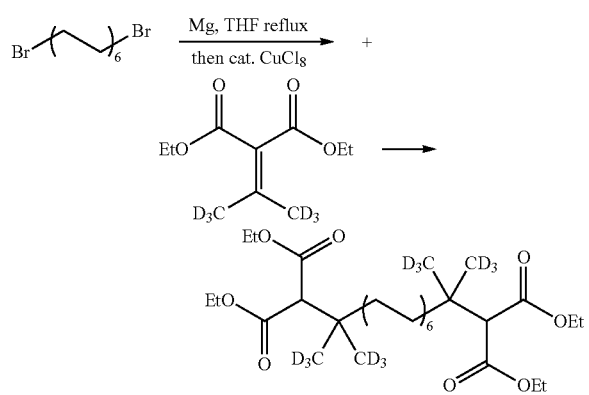

A 500-mL, 3-neck, round bottom flask equipped with a large magnetic stir bar, reflux condenser, thermometer, and a nitrogen inlet was flushed with nitrogen for 30 min. Into the flask was charged magnesium turnings (2.65 g, 109 mmoles), anhydrous THF (105 mL), and iodine crystals (~5-10 mg). The yellow mixture was heated to reflux (65° C.) using a temperature-controlled oil bath and was held at reflux until the yellow color of 12 had diminished (~30 min). A solution of 1,12-dibromododecane (16.2 g, 49.4 mmoles) in anhydrous THF (30 mL) was prepared. A portion of this solution (~4 mL) was added to the reaction, and heating was continued until evidence of reaction was seen (gas evolution, increased rate of reflux). The remaining solution was added dropwise over ~30 min, maintaining a gentle reflux. The reaction was refluxed for an additional 2 h. The reaction was cooled in an ice/salt bath (to −10° C.), CuCl(s) (0.35 g, 3.5 mmoles) was added, and the mixture was stirred for 15 min. A solution of diethyl isopropylidenemalonate (dimethyl-D6) (21.4 g, 104 mmoles) in anhydrous THF (22 mL) was added to the reaction dropwise at a rate to keep the temperature ≤5° C. (15-20 min). After an additional 5 min, the cold bath was removed. After the reaction temperature had risen to 15° C., the reaction was stirred an additional 1 h. The reaction was cooled to 0° C., and then a solution of 12N HCl(aq) (77 mL) in water (116 mL) was added in a slow stream. The mixture was extracted four times with Et2O (1×190 mL; 3×125 mL), and the combined Et2O extracts were washed with sat. NaHCO3(aq) (2×125 mL), water (1×125 mL), and sat. NaCl(aq) (1×125 mL). The Et2O layer was dried with MgSO4, filtered, and concentrated in vacuo to a crude oil (29.6 g), which was purified by flash chromatography (silica gel, EtOAc/hexanes gradient) to afford compound 4 precursor tetraester (D12) (15.8 g, 55% yield) as a pale, yellow oil.

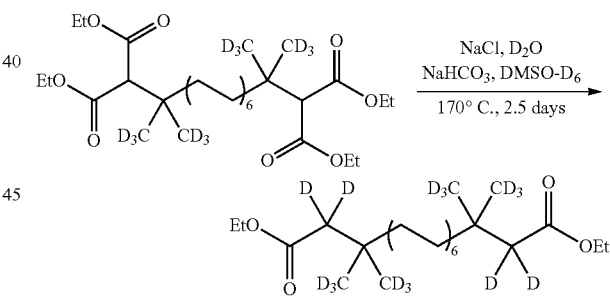

A 250-mL round bottom flask was equipped with a magnetic stir bar, reflux condenser (with no coolant flow) and an internal thermometer. A temperature-controlled oil bath was used for heating. Into the flask was charged compound 4 tetraester (D12) (15.8 g, 27.1 mmoles), DMSO-D6 (124 mL), D₂O (3.7 mL, 204 mmoles), NaCl(s) (4.0 g, 68.4 mmoles), and NaHCO3(s) (3.4 g, 40.5 mmoles). With stirring, the flask was heated in the oil bath set to 180° C. The reaction start time was noted when the internal temperature of the reaction rose to ≥154° C. The reaction was heated for 2.5 days. Ten drops of the reaction was shaken with 30 drops (0.6 mL) of 0.1M HCl(aq) and 0.5 mL of Et₂O. TLC of the Et₂O layer (10% EtOAc/hexanes; visualization with KMnO₄ stain) showed the reaction was complete. At intermediate stages of the reaction, a mixture of tetraester, triester (below) and desired diester was observed.

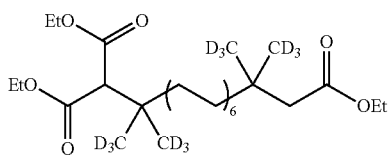

The reaction was allowed to cool to room temperature. The reaction was diluted with 0.1M HCl(aq) (500 mL) and extracted with Et$_2$O (3×230 mL). The Et2O extracts were combined and washed with water (1×150 mL) and saturated NaCl(aq) (1×150 mL). The Et$_2$O layer was dried with MgSO4, filtered, and concentrated in vacuo to an orange oil (11.1 g). The crude oil was chromatographed on silica gel using a DCM/hexanes gradient to obtain compound 4 Diester (D16) (8.8 g, 73% yield) as a pale, yellow oil. 1HNMR integration (in CDCl3/TMS) revealed that the methylenes alpha to the ester carbonyls were >90% enriched with deuterium.

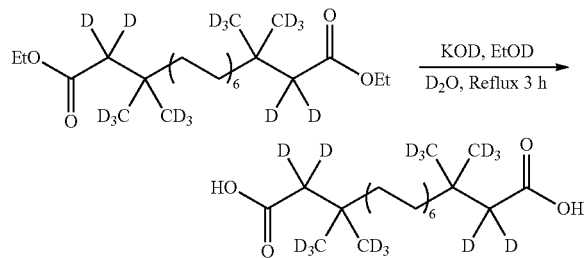

In a 500-mL round bottom flask equipped with a magnetic stir bar, reflux condenser, and a nitrogen line, compound 4 diester (D16) (8.8 g, 19.9 mmoles) and EtOD (250 mL) were stirred to a solution. 38% KOD/D$_2$O (66 g, 440 mmoles) was added, and the solution was refluxed for 3 h. Fifteen drops of the reaction was shaken with 15 drops of 1M HCl(aq) and 0.5 mL of Et2O. TLC of the Et$_2$O layer (silica gel plate; 7.5 mL DCM+2.5 mL hexanes+1 mL EtOH mobile phase; visualization with KMnO4 stain) showed the diester was consumed. The cooled reaction was diluted with D$_2$O (100 mL) and concentrated in vacuo until solids began to form. The mixture was stirred, and 12% DCl/D$_2$O was added portionwise (110 mL total) until the supernatant was acidic. The resulting warm mixture was stirred until it had cooled to room temperature. The mixture was filtered, and the solids were washed with H$_2$O (3×50 mL). The solids were dried in vacuo at 40° C. for 2 h. The solids were dissolved in MTBE (175 mL), and the solution was stirred with MgSO$_4$(s) and activated carbon (0.8 g) for 30 min. The slurry was filtered, and the filtrate was concentrated in vacuo to a white solid (7.4 g). The solid was dissolved in EtOH (100 mL) with warming to 50° C. With stirring, DI water (50 mL) was added slowly, and the resulting slurry was stirred for 1.5 h. The slurry was filtered, and the solids were washed with 50% EtOH(aq) (50 mL). The solids were dried in vacuo at 40° C. for 3 h to afford compound 4 (D16) (7.2 g; 93% yield) as a white solid which passed all release testing (HPLC chemical purity, mp, GCMS IE, 1HNMR, 13CNMR, KF).

Example 12: Process for the Preparation of 2,2,15,15-Tetramethyl(D12)-hexadecanedioic acid (Compound 7)

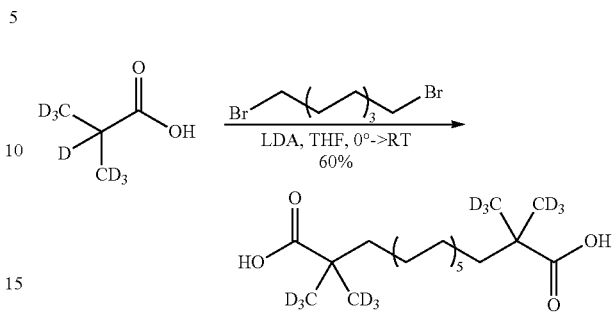

A 250-mL round bottom flask was equipped with a large magnetic stir bar, an internal temperature probe, and a nitrogen line. The apparatus was flushed thoroughly with nitrogen. Into the flask, lithium diisopropylamide solution (2.0M in heptanes/THF/ethylbenzene from Aldrich; 48 mL, 96 mmol) and anhydrous THF (40 mL) were charged. The solution was cooled to 0-5° C. with stirring. 85% Isobutyric acid (isopropyl-D7; contains 15 wt % ethyl ether, 5.2 g; 46 mmol) was added dropwise. The reaction was stirred for 5 min, the cold bath was removed, and the reaction was stirred an additional 1.5 h. The reaction was cooled to 0-5° C. A solution of 1,12-dibromododecane (5.7 g, 17.4 mmol) in anhydrous THF (15 mL) was added rapidly, and the reaction was stirred for 5 min. The cooling bath was removed, and the reaction was stirred at room temperature (15-20° C.) for 15-20 h. The disappearance of 1,12-dibromododecane was confirmed by silica gel TLC (100% hexanes eluent; KMnO4 (aq) visualization). The reaction was cooled to 0° C. 12% HCl(aq) (55 mL) was added slowly with swirling. Toluene (55 mL) was added, and the mixture was swirled until all solids had dissolved. The phases were separated, and the aqueous layer was extracted twice with toluene (30 mL each). The organic layers were combined and diluted to ~220 mL with toluene. The organic solution was washed with deionized water (65 mL), washed with saturated NaCl (aq) (65 mL), dried with MgSO4(s), filtered and concentrated in vacuo to a solid (8 g). The solid was taken up in hexanes (40 mL) and heated to 60° C. Insolubles were removed by filtration, and the filtrate was concentrated in vacuo to a solid. The solid was taken up in hexanes (40 mL) and heated to 60° C. to dissolve. The solution was stirred and allowed to cool slowly to room temperature. The resulting slurry was stirred for 2 h and then allowed to stand overnight. The slurry was filtered, and the solids were washed with hexanes (2×20 mL). The solid was air dried to obtain an off-white solid (4.3 g, 71% yield; impure compound 7 (D12) by HPLC analysis). The solid was dissolved in EtOH (22 mL) with warming to 45-50° C. With stirring, deionized water (22 mL) was added portionwise. The heating bath was removed, and the resulting slurry was stirred for 6 h. The slurry was filtered, and the solids were washed with 50% EtOH(aq) (25 mL). The solids were dried in vacuo at 40° C. for 16 h to obtain compound 7 (D12) (4.2 g, 69% yield) as a white solid.

Example 13: Process for the Preparation of 2,2,17,17-Tetramethyl(D12)-octadecanedioic acid (Compound 8)

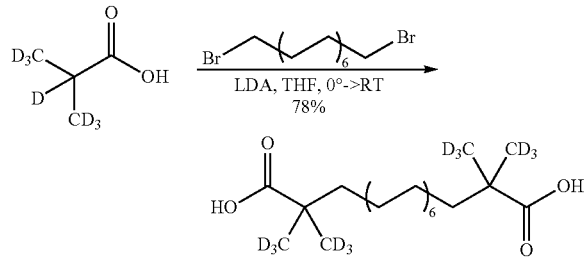

A 250-mL round bottom flask was equipped with a large magnetic stir bar, an internal temperature probe, and a nitrogen line. The apparatus was flushed thoroughly with nitrogen. Into the flask, lithium diisopropylamide solution (2.0M in heptanes/THF/ethylbenzene from Aldrich; 57 mL, 114 mmol) and anhydrous THF (46 mL) were charged. The solution was cooled to 0-5° C. with stirring. 85% Isobutyric acid (ISOPROPYL-D7; contains 15 wt % ethyl ether, 6.3 g; 56.3 mmol) was added dropwise. The reaction was stirred for 5 min, the cold bath was removed, and the reaction was stirred an additional 1.5 h. The reaction was cooled to 0-5° C. A solution of 1,14-dibromotetradecane (7.4 g, 20.8 mmol) in anhydrous THF (15 mL) was added rapidly, and the reaction was stirred for 5 min. The cooling bath was removed, and the reaction was stirred at room temperature (15-20° C.) for 15-18 h. The disappearance of 1,14-dibromotetradecane was confirmed by silica gel TLC (100% hexanes eluent; $KMnO_4$(aq) visualization). The reaction was cooled to 0° C. 12% HCl(aq) (65 mL) was added slowly with swirling. Toluene (65 mL) was added, and the mixture was swirled until all solids had dissolved. The phases were separated using a separatory funnel. The aqueous layer was extracted twice with toluene (30 mL each). The organic layers were combined and were diluted to ~300 mL with toluene. The organic solution was washed with deionized water (100 mL), washed with saturated NaCl(aq) (100 mL), dried with $MgSO_4$(s), filtered and concentrated in vacuo to a solid (7.9 g). The solid was taken up in hexanes (55 mL) and heated to 60° C. to dissolve. The solution was stirred and allowed to cool slowly to room temperature. The resulting slurry was stirred for 2 h and then allowed to stand overnight. The slurry was filtered, and the solids were washed with hexanes (20 mL). The solid was air-dried to obtain an off white solid (6.4 g, 80% yield; impure compound 8 (D12) by HPLC analysis). The solid was dissolved in EtOH (33 mL) with warming to 40-45° C. With stirring, deionized water (33 mL) was added portionwise. The heating bath was removed, and the resulting slurry was stirred for 6 h. The slurry was filtered, and the solids were washed with 50% EtOH(aq) (25 mL). The solids were dried in vacuo at 40° C. for 16 h to obtain compound 8 (D12) (6.2 g, 78% yield) as a white solid.

Example 14: Stability of Compounds of the Invention

The objective of this stability study is to measure the chemical and isotopic stability of the compounds shown below as solutions in DMSO/phosphate buffered saline solution over a 48 hour period, with time points at 2, 4, 24 and 48 hours.

Compounds:

| Compound | $R_1$ | $R_2$ | $R_3$ | $R_4$ | $R_5$ | $R_6$ | $R_7$ | $R_8$ | n |
|---|---|---|---|---|---|---|---|---|---|
| 1/T1 | D | D | D | D | $CD_3$ | $CD_3$ | $CD_3$ | $CD_3$ | 10 |
| 2/T2 | D | D | D | D | $CH_3$ | $CH_3$ | $CH_3$ | $CH_3$ | 10 |
| 3/T3 | H | H | H | H | $CD_3$ | $CD_3$ | $CD_3$ | $CD_3$ | 10 |
| 4/T4 | D | D | D | D | $CD_3$ | $CD_3$ | $CD_3$ | $CD_3$ | 12 |
| 5/T5 | D | D | D | D | $CH_3$ | $CH_3$ | $CH_3$ | $CH_3$ | 12 |
| 6/T6 | H | H | H | H | $CD_3$ | $CD_3$ | $CD_3$ | $CD_3$ | 12 |
| 7/T7 | $CD_3$ | $CD_3$ | $CD_3$ | $CD_3$ | H | H | H | H | 10 |
| 8/T8 | $CD_3$ | $CD_3$ | $CD_3$ | $CD_3$ | H | H | H | H | 12 |

General Procedure

A 1 mg/mL stock solution (~55 mL) of deuterated compound in DMSO was prepared. A measured volume of stock (7.5 mL) was dispensed in to each of seven vials. To each vial was added a measured volume of PBS (aq) (3.0 mL), and each vial was agitated to mix. The vials were then placed in a thermostatically-controlled oven set to 37° C. At each time-point (0 h, 2 h, 4 h, 24 h, 48 h) a vial was drawn from the oven. To the vial was added MTBE (9.0 mL), and the mixture was stirred vigorously for 5 min. The layers were separated, and the MTBE layer was agitated with DI water (3.75 mL) for 1 min. The layers were separated. The MTBE layer was dried with $MgSO_4$ for >1 h, and then filtered through a PTFE syringe filter into a tared vial. The solution was concentrated in vacuo to a solid residue, and the mass of the residue was calculated and recorded. To the residue a measured volume of MeOH was added to make (theoretically) a 2.5 mg/mL solution. In this case, 3.00 mL MeOH was added to each vial which theoretically contained 7.5 mg of compound. The content of each solution was measured by quantitative HPLC analysis (by comparison to a standard of known concentration). The MeOH solutions were then recovered, concentrated in vacuo to a solid, and then analyzed by GCMS to determine isotopic enrichment as the methyl ester derivatives.

Results

HPLC analyses of each sample were carried out; an assay against a freshly prepared standard to determine the recovery and an area percent analysis to determine the chemical purity of the recovered material with respect to similar compounds.

| Compound 1/T1 (D16) Stability Data | | | | | |
|---|---|---|---|---|---|
| Stock Preparation | | | | | |
| Mass of Sample: | | | 55.9 mg | | |
| Vol DMSO: | | | 56.0 mL | | |
| Stock Concentration: | | | 0.998 mg/mL | | |
| Sample ID | Concentrated Mass | HPLC Assay | Corrected Mass Recovery | HPLC Area Percentage | GC/MS IE |
| T1-0 h | 10.3 mg | 66.5% | 6.9 mg | 98.1% | 98.3% |
| T1-2 h | 10.9 mg | 64.5% | 7.0 mg | 97.2% | 98.2% |

Compound 1/T1 (D16) Stability Data

| | | | | | |
|---|---|---|---|---|---|
| T1-4 h | 10.0 mg | 70.1% | 7.0 mg | 97.8% | 98.2% |
| T1-24 h | 7.8 mg | 89.3% | 7.0 mg | 97.6% | 98.3% |
| T1-48 h | 8.1 mg | 86.3% | 7.0 mg | 97.5% | 98.3% |
| | | | Original Sample | 100.0% | 98.3% |

The results for Compound 1/T1 show that the analyte was recovered in over 90% yield with a chemical purity of around 97% with respect to related substances detectable in the HPLC system. No disenrichment of the product was observed throughout the time period of the study.

Compound 2/T2 2(D4) Stability Data Batch # 10-163-13-13

Stock Preparation

| | |
|---|---|
| Mass of Sample: | 59.5 mg |
| Vol DMSO: | 60.0 mL |
| Stock Concentration: | 0.992 mg/mL |

| Sample ID | Concentrated Mass | HPLC Assay | Corrected Mass Recovery | HPLC Area Percentage | GC/MS IE |
|---|---|---|---|---|---|
| T2-0 h | 10.3 mg | 67.4% | 6.9 mg | 94.9% | 97.9% |
| T2-2 h | 10.4 mg | 65.1% | 6.8 mg | 95.5% | 98.0% |
| T2-4 h | 11.0 mg | 62.4% | 6.9 mg | 95.4% | 98.0% |
| T2-24 h | 8.2 mg | 86.0% | 7.0 mg | 95.2% | 98.0% |
| T2-48 h | 2.5 mg* | 280.4%* | 7.0 mg | 96.0% | 98.0% |
| T2-96 h | 9.2 mg | 76.8% | 7.1 mg | 96.1% | 98.0% |
| | | | Original Sample† | 97.0% | |

The results for Compound 2/T2 show that the analyte was recovered in approximately 90% yield with a chemical purity of around 96% with respect to related substances detectable in the HPLC system. No disenrichment of the product was observed throughout the time period of the study.

Compound 3/T3 (D12) Stability Data Batch # PR-22093

Stock Preparation:

| | |
|---|---|
| Mass of Sample: | 60.4 mg |
| Vol DMSO: | 60.0 mL |
| Stock Concentration: | 1.007 mg/mL |

| Sample ID | Concentrated Mass | HPLC Assay | Corrected Mass Recovery | HPLC Area Percentage | GC/MS IE |
|---|---|---|---|---|---|
| T3-0 h | 21.4 mg | 33.3% | 7.1 mg | 98.0% | 99.9% |
| T3-2 h | 18.9 mg | 38.4% | 7.3 mg | 98.8% | 99.9% |
| T3-4 h | 22.4 mg | 32.4% | 7.3 mg | 98.4% | 99.9% |
| T3-24 h | 16.1 mg | 46.0% | 7.4 mg | 98.6% | 99.9% |
| T3-48 h | 14.4 mg | 50.2% | 7.2 mg | 98.5% | 99.9% |
| | | | Original Sample† | 100.0% | |

The results for Compound 3/T3 are very similar to those obtained for Compound 2. The material was recovered at about 95% yield and area percent chemical purity was between 98% and 99% for all samples through the study. No disenrichment was observed.

Compound 4/T4 4(D16) Stability Data

Stock Preparation:

| | |
|---|---|
| Mass of Sample: | 52.8 mg |
| Vol DMSO: | 52.5 mL |
| Stock Concentration: | 1.086 mg/mL |

| Sample ID | Concentrated Mass | HPLC Assay | Corrected Mass Recovery | HPLC Area Percentage | GC/MS IE |
|---|---|---|---|---|---|
| T4-0 h | 10.0 mg | 70.9% | 7.1 mg | 97.2% | 98.6% |
| T4-2 h | 10.7 mg | 65.9% | 7.1 mg | 97.8% | 98.4% |
| T4-4 h | 11.0 mg | 53.8% | 5.9 mg | 97.5% | 98.4% |
| T4-24 h | 7.2 mg | 93.8% | 6.8 mg | 96.5% | 98.4% |
| T4-48 h | 9.0 mg | 77.6% | 7.0 mg | 97.5% | 98.3% |
| | | | Original Sample | 99.2% | 98.3% |

The results for Compound 4/T4 were essentially the same as those for Compound 1.

Compound 5/T5 5(D4) Stability Data Batch # 10-163-14-19

Stock Preparation:

| | |
|---|---|
| Mass of Sample: | 56.5 mg |
| Vol DMSO: | 56.0 mL |
| Stock Concentration: | 1.009 mg/mL |

| Sample ID | Concentrated Mass | HPLC Assay | Corrected Mass Recovery | HPLC Area Percentage | GC/MS IE |
|---|---|---|---|---|---|
| T5-0 h | 12.7 mg | 57.0% | 7.2 mg | 98.4% | 96.3% |
| T5-2 h | 16.5 mg | 44.6% | 7.4 mg | 98.0% | 95.9% |
| T5-4 h | 16.0 mg | 46.3% | 7.4 mg | 98.5% | 96.0% |
| T5-24 h | 7.8 mg | 95.3% | 7.4 mg | 98.4% | 96.0% |
| T5-48 h | 3.4 mg* | 213.8%* | 7.3 mg | 98.0% | 95.5% |
| T5-96 h | 9.2 mg | 79.8% | 7.3 mg | 98.7% | 96.1% |
| | | | Original Sample† | 100.0% | |

The results for Compound 5/T5 are very similar to those obtained for the other Compound compounds. The material was recovered at about 95% yield and area percent chemical purity was between 98% and 99% for all samples through the study. No disenrichment was observed, although it appears that this compound was slightly disenriched when compared with the other compounds in the set.

Compound 6/T6 (D12) Stability Data Batch # 10-163-15-18

Stock Preparation:

| | |
|---|---|
| Mass of Sample: | 55.9 mg |
| Vol DMSO: | 56.0 mL |
| Stock Concentration: | 0.998 mg/mL |

| Sample ID | Concentrated Mass | HPLC Assay | Corrected Mass Recovery | HPLC Area Percentage | GC/MS IE |
|---|---|---|---|---|---|
| T6-0 h | 18.2 mg | 39.0% | 7.1 mg | 98.4% | 99.2% |
| T6-2 h | 21.8 mg | 33.1% | 7.2 mg | 98.6% | 99.0% |
| T6-4 h | 19.5 mg | 35.6% | 6.9 mg | 97.9% | 99.1% |
| T6-24 h | 18.1 mg | 39.8% | 7.2 mg | 98.5% | 99.0% |
| T6-48 h | 12.0 mg | 59.6% | 7.1 mg | 98.7% | 99.1% |
| | | | Original Sample† | 100.0% | |

The results for Compound 6/T6 are very similar to those of the other compounds. The material was recovered at about 95% yield and area percent chemical purity was between 98% and 99% for all samples through the study. No disenrichment was observed.

| Compound 7/T7 (D12) Stability Data | | | | |
|---|---|---|---|---|
| Stock Preparation | | | | |
| Mass of Sample: | | 41.8 mg | | |
| Vol DMSO: | | 42.0 mL | | |
| Stock Concentration: | | 0.995 mg/mL | | |
| Sample ID | Concentrated Mass | HPLC Assay | Corrected Mass Recovery | HPLC Area Percentage | GC/MS IE |
| T7-0 h | 5.0 mg | 89.4% | 4.5 mg | 96.8% | 99.9% |
| T7-2 h | 4.5 mg | 101.6% | 4.6 mg | 95.4% | 99.9% |
| T7-4 h | 4.9 mg | 91.6% | 4.5 mg | 95.8% | 99.9% |
| T7-24 h | 4.9 mg | 92.3% | 4.5 mg | 96.9% | 99.9% |
| T7-48 h | 5.5 mg | 82.2% | 4.5 mg | 96.7% | 99.9% |
| Original Sample | | | | 99.5% | 99.9% |

The results for Compound 7/T7 show that the analyte was recovered in approximately 90% yield with a chemical purity of around 96% with respect to related substances detectable in the HPLC system. No disenrichment of the product was observed throughout the time period of the study.

| Compound 8/T8 (D12) Stability Data | | | | |
|---|---|---|---|---|
| Stock Preparation: | | | | |
| Mass of Sample: | | 39.6 mg | | |
| Vol DMSO: | | 40.0 mL | | |
| Stock Concentration: | | 0.990 mg/mL | | |
| Sample ID | Concentrated Mass | HPLC Assay | Corrected Mass Recovery | HPLC Area Percentage | GC/MS IE |
| T8-0 h | 6.9 mg | 60.0% | 4.1 mg | 95.1% | 99.9% |
| T8-2 h | 6.0 mg | 68.7% | 4.1 mg | 94.3% | 99.9% |
| T8-4 h | 7.3 mg | 56.9% | 4.2 mg | 94.1% | 99.9% |
| T8-24 h | 6.4 mg | 66.8% | 4.3 mg | 96.0% | 99.9% |
| T8-48 h | 9.3 mg | 47.7% | 4.4 mg | 97.2% | 99.9% |
| Original Sample | | | | 100.0% | 99.9% |

The results for Compound 8/T8 are very similar to those obtained for Compound 7. The material was recovered at about 85% yield and area percent chemical purity was around 95% for all samples through the study. No disenrichment was observed.

Conclusion

Based on the data shown above, there appeared to be no chemical degradation of the compounds studied during the timescale of the study (48 h). No disenrichment of any of the compound was observed during the time course of the study.

Example 15: Comparative Oral Bioavailability Study

The pharmacokinetic properties and the oral bioavailability were investigated for the following comparative compounds:

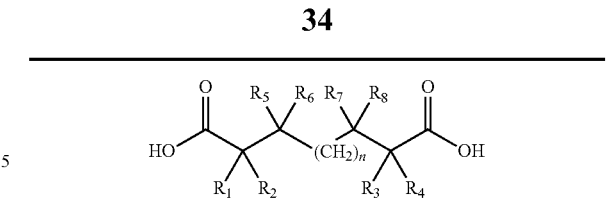

| Compound | $R_1$ | $R_2$ | $R_3$ | $R_4$ | $R_5$ | $R_6$ | $R_7$ | $R_8$ | n |
|---|---|---|---|---|---|---|---|---|---|
| 1 | D | D | D | D | $CD_3$ | $CD_3$ | $CD_3$ | $CD_3$ | 10 |
| 1" | H | H | H | H | $CH_3$ | $CH_3$ | $CH_3$ | $CH_3$ | 10 |
| 7 | $CD_3$ | $CD_3$ | $CD_3$ | $CD_3$ | H | H | H | H | 10 |
| 7" | $CH_3$ | $CH_3$ | $CH_3$ | $CH_3$ | H | H | H | H | 10 |

Definitions $t_{1/2}$ Apparent terminal elimination half-life $\{t_{1/2}=\ln(2)/\lambda_z\}$ $t_{max}$ Time of maximum plasma concentration measured $(C_{max})$ $C_{max}$ Maximum plasma concentration measured, occurring at $t_{max}$ $AUC_{inf}$ Area under the plasma concentration-time curve from time zero (the time of dosing) extrapolated to infinity $C_0$ Back-extrapolated concentration at time zero (only for IV administration)

Vc Central volume of distribution (only for IV administration)

Vss Volume of distribution estimated for the steady state phase

Cl Total body clearance (only for IV administration)

$MRT_{inf}$ Mean residence time

F Oral bioavailability $(AUC_{PO}*dose_{IV})/(AUC_{IV}*dose_{PO})*100$

The plasma concentrations of the test items were measured by LC/MS/MS method following single intravenous and oral administration at the doses of 5 mg/kg body weight and 50 mg/kg body weight, respectively. Following intravenous administration small inter-individual variability was observed. Following i.v administration, the highest plasma concentrations were measured at the first sampling timepoint (5 minutes) followed by a biphasic continuous decrease. Following oral administration, t(he absorption process was prolonged and showed high individual variability. The variability was smaller for the deuterated analogues than for the non-deuterated compounds. The peaks $(t_{max})$ occurred at 4 hours post-dose for each Compound 1 and Compound 7 treated rats. Contrary, $t_{max}$ varied from 0.5 to 12 hours for the Compound 7" and Compound 1" administered animals. The pharmacokinetic parameters were calculated using non-compartmental analysis. All plasma level curves were characterized well since the extrapolated parts were small and the fit of the terminal phases was good. The peak concentrations, $t_{max}$ and the apparent terminal elimination half-lives $(t_{1/2})$ were the followings:

| | Mean CV (%) | | | | |
|---|---|---|---|---|---|
| | 5 mg/kg iv dose | | 50 mg/kg po dose | | |
| Compound | $C_0$ [µg/ml] | $t_{1/2}$ [h] | $C_{max}$ [µg/ml] | $t_{max}$ [h] | $t_{1/2}$ [h] |
| 7" | 74.6 (6.9%) | 2.18 (19.1%) | 143 (41.3%) | 8 (50.0%) | 2.22 (9.9%) |
| 1" | 56.1 (6.2%) | 2.68 (6.0%) | 103 (24.2%) | 3.5 (79.5%) | 2.43 (57.6%) |
| 1 | 67.0 (8.8%) | 2.81 (28.5%) | 114 (19.6%) | 4 (0%) | 4.29 (15.7%) |
| 7 | 64.3 (16.9%) | 2.14 (2.6%) | 151 (29.0%) | 4 (0%) | 6.64 (50.3%) |

All experimental compound analogues showed small volume of distribution (Vc: 67.2-89.4 mg/kg; Vss: 97.3-143 ml/kg) (approximately equal to total blood volume), and clearance (Cl: 23.2-42.0 h*µg/ml).

Following administration of the same intravenous or oral dose among the 1, 1", 7, 7" compounds, compound 7 showed the highest total exposure:

| | Mean CV (%) $AUC_{inf}$ [h * µg/ml] | |
|---|---|---|
| Compound | 5 mg/kg iv | 50 mg/kg po |
| 7" | 128 (13.4%) | 1586 (28.3%) |
| 1" | 124 (23.6%) | 863 (29.4%) |
| 1 | 137 (19.3%) | 1246 (11.1%) |
| 7 | 218 (14.9%) | 2221 (36.8%) |

The oral bioavailability of all analogues indicated good absorption The oral bioavailability for the investigated compounds were the following:

| Compound | Mean (CV %) F [%] |
|---|---|
| 7" | 124 (28.3) |
| 1" | 69.6 (29.4) |
| 1 | 91.0 (11.1) |
| 7 | 102 (36.8) |

The deuterated/non-deuterated ratios were calculated for the most important pharmacokinetic parameters. After 5 mg/kg intravenous dosing the kinetic parameters of Compound 1" and Compound 1 did not show biologically relevant differences. For Compound 7 the tendency of the slower elimination already could be observed which resulted in higher total exposure, longer mean residence time and smaller clearance compared to its non-deuterated analogue.

| Deuterated/Non Deuterated ratio 5 mg/kg iv dose | For $AUC_{inf}$ (hr * µg/ml) | For Cl (ml/hr/kg) [%] | For $MRT_{inf}$ (hr) |
|---|---|---|---|
| 1/1" | 110 | 89 | 100 |
| 7/7" | 170 | 58 | 168 |

Following 50 mg/kg oral administration the absorption did not show differences since the peak concentrations were almost equal for the deuterated and the non-deuterated analogues. Increased total exposure and the prolonged mean residence time were obtained for both Compound 1 and Compound 7 due to the slower elimination. The effect was more expressed for Compound 7 than for Compound 1.

| Deuterated/Non Deuterated ratio 50 mg/kg po dose | For $t_{1/2}$ (hr) | For $C_{max}$ (µg/ml) | For $AUC_{inf}$ (hr * µg/ml) [%] | For $MRT_{inf}$ (hr) |
|---|---|---|---|---|
| 1/1" | 177 | 111 | 144 | 115 |
| 7/7" | 300 | 106 | 140 | 133 |

Preparation of Vehicle

The vehicle for oral administration was prepared in advance. Preparation: 1 g of carboxymethylcellulose sodium salt was dissolved in 100 ml of Humaqua. The vehicle was prepared at least 2 days prior to formulation of the test items. The vehicle was stored in a refrigerator when not in use.

Preparation of the Dose Forms

Intravenous Formulation

The required amount of test item was weighed on an analytical balance, transferred into a suitable vial. The test item was dissolved in the required volume of N,N-dimethylacetamide (40% of the final volume). Dissolution of the test item was facilitated by gentle mixing by vortex. The solution was diluted with the suitable volume of PEG400 (40% of the final volume) then Salsol A (20% of the final volume). The final concentration of the test item in the solution was 5 mg/ml. The formulations were prepared freshly on the day of administration.

Oral Dose Form:

The required amount of test item was weighed on an analytical balance, transferred into a test tube and mixed with the suitable volume of 1% CMC to achieve the final concentration of 25 mg/ml. The suspension was sonicated twice in bath sonicator for 30 min at 40 C (each round), and left overnight at room temperature. On the following day, the suspension was sonicated again (bath sonicator, 30 min, 40° C.) and further homogenized in a glass/glass homogenizer trying to reaching an homogenous suspension. In spite of the above procedure the quality (homogeneity) of the suspension was not perfect. The suspension was stored at room temperature till administration.

Animal Specification

Species/Strain rat/Wistar (Crl:(WI)BR rats)
Number of animals: 24 males (at least 32 for cannulation*)
Body weights at arrival: 250-270 g
Acclimatization: at least five days Experimental Study Cannulation After the acclimatization period, rats were equipped with a jugular vein cannula under isoflurane anesthesia. The following day the animals were used for the study. In the morning the rats were checked for health status and blood sampling before assigning them into the experimental group. If the cannula did not function properly, the animal was left out from the experiment.

Plasma Concentrations

Following intravenous administration small inter-individual variability was observed. The highest plasma concentrations were measured at the first sampling time-point (5 minutes). Then the concentrations decreased continuously. In the semi-logarithmic curves biphasic decrease could be seen. Following oral administration the absorption process was prolonged and showed high individual variability. The variability was smaller for the deuterated analogues than for the non-deuterated compounds. The peaks occurred at 4 hours post-dose for each Compound 1 and Compound 7 treated rats. Contrary, tmax varied from 0.5 to 12 hours for the Compound 7" and Compound 1" administered animals.

Pharmacokinetic Evaluation

The terminal elimination phase was defined on the basis of the last 3-5 measured concentration except rat A4. The good regression data indicated that the reliable terminal half-lives could be determined. For rat A4 the peak concentration occurred at 12 hours post-dose, thus only 1 later time point was available for calculation of the half-life. All experimental compound analogues showed small distribution volume. The central volume of distribution (Vc: 67.2-89.4 mg/kg) was approximately equal to the total blood volume. The volume of distribution estimated for the steady state situation (Vss: 97.3-143 ml/kg) remained also small compared to the total extracellular fluid volume (~300 ml/kg). The clearance was also very small for all experimental compound analogues. The smallest clearance was obtained for Compound 7: 23.2 ml/h/kg. Thus, the longest mean residence time was also observed for Compound 7: 4.2 h and 11.8 h following intravenous and oral administration, respectively.

Conclusions

Figure 1B:
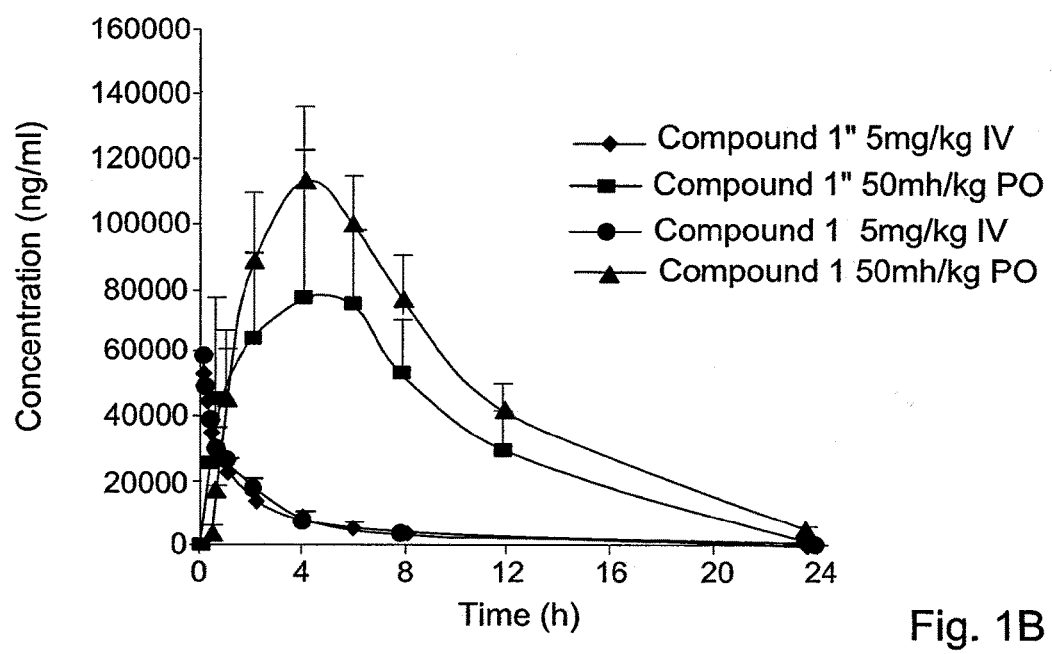
Figure 2:
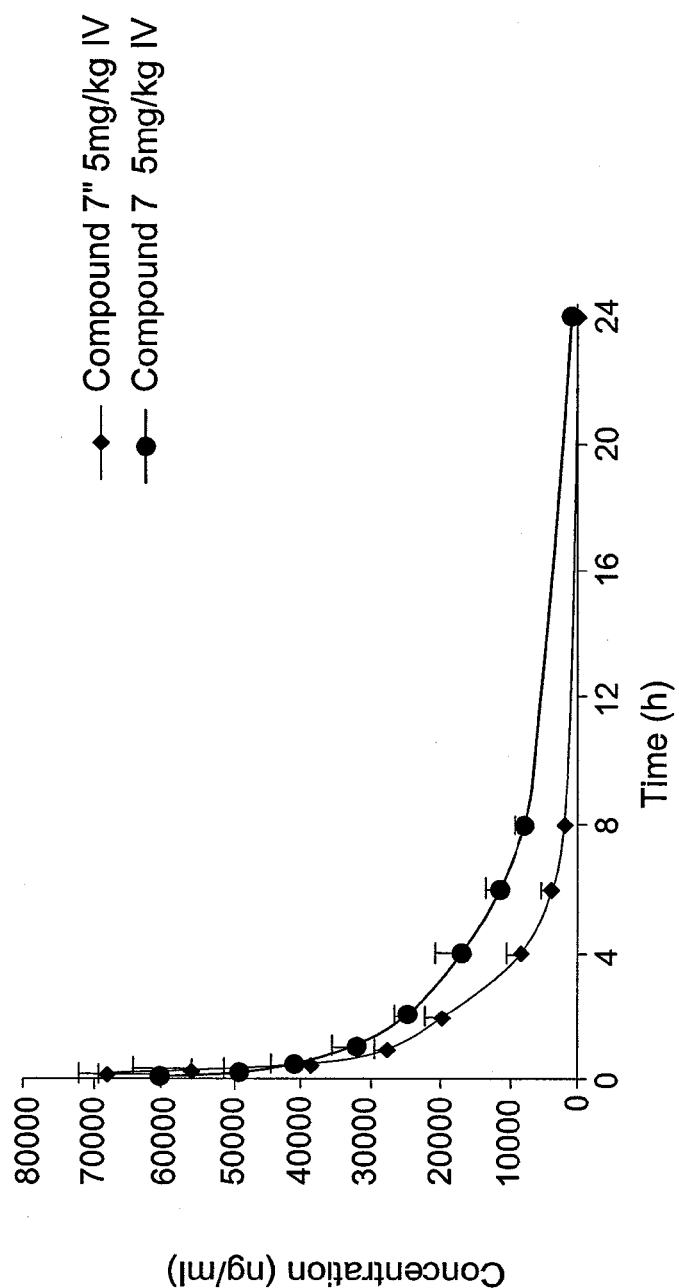
FIG. 2 shows the mean plasma levels curves (with S.D.) of compounds 7" and 7 (5 mg/kg body weight administered iv).

Pharmacokinetic properties of Compound 7" and Compound 1" were compared to those of their deuterated analogues, Compound 7 and Compound 1, respectively. The mean plasma level curves (with S.D.) for the pairs are shown in FIGS. 1A-1B and FIG. 2.

The deuterated/non-deuterated ratios were calculated for the most important pharmacokinetic parameters. After 5 mg/kg intravenous dosing the kinetic parameters of Compound 1" and Compound 1 did not show biologically relevant differences.

Although the calculated apparent terminal elimination half life for Compound 7 did not differ from that of Compound 7", the plasma level curve already indicated the tendency of the slower elimination which resulted in higher total exposure, longer mean residence time and smaller clearance compared to its non-deuterated analogue.

Following 50 mg/kg oral administration the absorption did not show differences since the peak concentrations were almost equal for the deuterated and the non-deuterated analogues. Implementation of deuterium atoms into the molecules resulted in increased total exposure and the prolonged mean residence time for both Compound 1 and Compound 7 due to the slower elimination. The effect was more expressed for Compound 7 than for Compound 1.

Example 16: Comparative In Vivo Efficacy Studies

Animal Model:

Male db/db Mouse Model. Age of animal at start of treatment: 10-11 weeks. Animals per treatment group: 6-7 mice per each group.

Treatment Groups:
Vehicle control: (1% CMC in water).
Positive control: Rosiglitazone, 25 mg/kg.
Group I: Compound 7", 12.5 mg/kg.
Group II: Compound 7", 25 mg/kg.
Group III: Compound 7, 12.5 mg/kg.
Group IV: Compound 7, 25 mg/kg.

Duration of treatment: 15 days.

Study Summary:

1. Dosing: Animals are 10-11 weeks of age and were allowed to acclimate 1-2 weeks. After acclimation, animals were entered to the study and were averaged daily for a duration of 15 days.
2. Formulation: compounds were formulated with CMC in 1% water. Formulation also involve sonication and vortexing before use.
3. Body Weight: Body weight was followed throughout the study to monitor animal health.
4. Fasting Glucose Levels: 3 h-Fasting glucose levels were measured on tail blood of all the animals on days 0, 6, 12, and 16 (not shown) of the study using glucose sticks (Proforma).
5. Triglycerides: Blood samples are collected on all animals on termination of the study, and analyzed for triglycerides.
6. Insulin Levels: Blood samples are collected on all animals on termination of the study, and analyzed for plasma insulin using RIA.
7. Necropsy: Animals are sacrificed after 15 days of drug treatment. Gross pathology evaluation of the liver is assessed at the time of necropsy.

Figure 3:
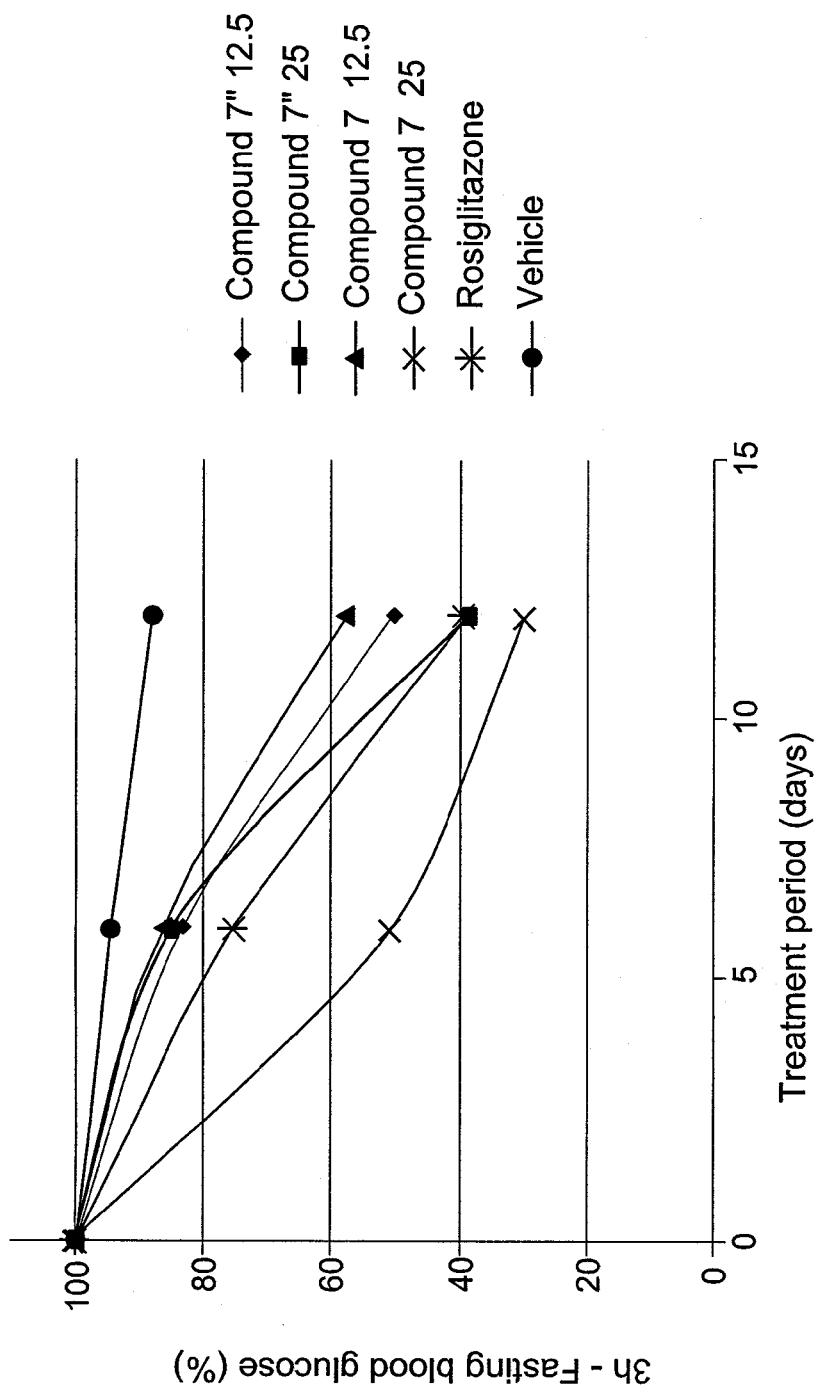
FIG. 3 shows the 3 h-fasting blood glucose (%) of each treatment group at 0, 6 and 12 days of treatment (note that 100% of 3 h-Fasting blood glucose equals to 349±17 mg %)

Results:

FIG. 3 shows the 3 h-fasting blood glucose (%) of each treatment group at 0, 6 and 12 days of treatment (note that 100% of 3 h-Fasting blood glucose equals to 349±17 mg %). The results show that treatment Group IV (Compound 7, 25 mg) showed greater efficacy as compared with Rosiglitazone (the current state of the art treatment for Diabetes), achieving higher rate of decrease in glucose levels to normalized plasma levels (less than 110 mg % of glucose). Furthermore, the efficacy of treatment Group III (Compound 7, 25 mg dose) exceeds that of both treatment Groups I and II (Compound 7").

The invention claimed is:

1. A deuterium enriched composition of a compound of general formula (I), including any salts, esters or anhydrides thereof:

$$\underset{HO}{\overset{O}{\underset{\|}{C}}}-\underset{R_2}{\overset{R_1}{\underset{|}{C}}}-\underset{R_6}{\overset{R_5}{\underset{|}{C}}}-L-\underset{R_8}{\overset{R_7}{\underset{|}{C}}}-\underset{R_4}{\overset{R_3}{\underset{|}{C}}}-\underset{OH}{\overset{O}{\underset{\|}{C}}} \qquad (I)$$

wherein
L is a straight or branched $C_8$-$C_{16}$ alkylene; optionally interrupted by at least one moiety selected from O, S, NH, $C_5$-$C_{10}$cycloalkylene, $C_5$-$C_{10}$cycloheteroalkylene, $C_6$-$C_{18}$ arylene, $C_6$-$C_{18}$ heteroarylene;
each of $R_1$-$R_8$ is independently selected from H, D, $CH_3$ and $CD_3$; wherein at least one of $R_1$-$R_8$ is D or $CD_3$; and
the abundance of deuterium at any D- or $CD_3$-occupied position in the compound of the composition is substantially greater than the 0.015% natural abundance of deuterium.

2. A deuterium enriched composition according to claim 1, wherein said compound of general formula (I), including any salts, esters or anhydrides thereof is:

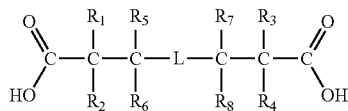

(I)

wherein
L is a straight or branched $C_8$-$C_{16}$ alkylene; optionally interrupted by at least one moiety selected from O, S, NH, $C_5$-$C_{10}$cycloalkylene, $C_5$-$C_{10}$cycloheteroalkylene, $C_6$-$C_{18}$ arylene, $C_6$-$C_{18}$ heteroarylene;
each of $R_1$-$R_4$ is independently H or D;
each of $R_5$-$R_8$ is independently $CH_3$ or $CD_3$;
wherein when $R_1$-$R_4$ are H, at least one of $R_5$-$R_8$ is $CD_3$; or when $R_5$-$R_8$ are $CH_3$, at least one of $R_1$-$R_4$ is D.

3. A deuterium enriched composition according to claim 1, wherein said compound of general formula (I), including any salts, esters or anhydrides thereof is:

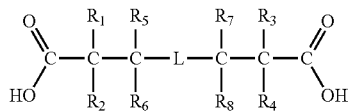

(I)

wherein
L is a straight or branched $C_8$-$C_{16}$ alkylene; optionally interrupted by at least one moiety selected from O, S, NH, $C_5$-$C_{10}$ cycloalkylene, $C_5$-$C_{10}$ cycloheteroalkylene, $C_6$-$C_{18}$ arylene, $C_6$-$C_{18}$ heteroarylene;
each of $R_1$-$R_4$ is independently $CH_3$ or $CD_3$, and at least one of $R_1$-$R_4$ is $CD_3$; and
each of $R_5$-$R_8$ is independently H.

4. A deuterium enriched composition according to claim 1, wherein, in said compound, at least one of $R_1$-$R_4$ is D.

5. A deuterium enriched composition according to claim 1, wherein, in said compound, at least one of $R_5$-$R_8$ is $CD_3$.

6. A deuterium enriched composition according to claim 1, wherein, in said compound, at least one of $R_1$-$R_4$ is $CD_3$.

7. A deuterium enriched composition according to claim 1, wherein, in said compound, at least one of $R_5$-$R_8$ is D.

8. A deuterium enriched composition according to claim 1, wherein, in said compound, L is any one of —$(CH_2)_{10}$— and —$(CH_2)_{12}$—.

9. A deuterium enriched composition according to claim 1, wherein, in said compound, at least one of $R_1$-$R_4$ is D and at least one of $R_5$-$R_8$ is $CD_3$.

10. A deuterium enriched composition according to claim 1, wherein, in said compound, at least one of $R_1$-$R_4$ is $CD_3$ and at least one of $R_5$-$R_8$ is D.

11. A deuterium enriched composition according to claim 1, wherein said compound is:

| Compound | $R_1 = R_2 = R_3 = R_4$ | $R_5 = R_6 = R_7 = R_8$ |
|---|---|---|
| II | D | $CH_3$ |
| III | H | $CD_3$ |
| IV | D | $CD_3$. |

12. A deuterium enriched composition according to claim 1, wherein said compound is:

| Compound | $R_1 = R_2$ | $R_3 = R_4$ | $R_5 = R_6$ | $R_7 = R_8$ |
|---|---|---|---|---|
| V | D | H | $CH_3$ | $CH_3$ |
| VI | D | H | $CD_3$ | $CH_3$ |
| VII | D | H | $CH_3$ | $CD_3$ |
| VIII | D | H | $CD_3$ | $CD_3$ |
| IX | D | D | $CD_3$ | $CH_3$. |

13. A deuterium enriched composition according to claim 1, wherein said compound is:

| Compound | $R_1 = R_3$ | $R_2 = R_4$ | $R_5 = R_6$ | $R_7 = R_8$ |
|---|---|---|---|---|
| X | D | H | $CH_3$ | $CH_3$ |
| XI | D | H | $CD_3$ | $CH_3$ |
| XII | D | H | $CD_3$ | $CD_3$. |

14. A deuterium enriched composition according to claim 1, wherein said compound is:

| Compound | $R_1 = R_3$ | $R_2 = R_4$ | $R_5 = R_7$ | $R_6 = R_8$ |
|---|---|---|---|---|
| XIII | D | H | $CH_3$ | $CH_3$. |

15. A deuterium enriched composition according to claim 1, wherein said compound is:

| Compound | $R_1 = R_2 = R_3 = R_4$ | $R_5 = R_6 = R_7 = R_8$ |
|---|---|---|
| XIV | $CD_3$ | H. |

16. A deuterium enriched composition according to claim 1, wherein said compound is:

| Compound | $R_1 = R_2$ | $R_3 = R_4$ | $R_5 = R_6$ | $R_7 = R_8$ |
|---|---|---|---|---|
| XV | $CD_3$ | $CH_3$ | H | H. |

17. A deuterium enriched composition according to claim 1, wherein said compound is:

| Compound | $R_1 = R_3$ | $R_2 = R_4$ | $R_5 = R_6$ | $R_7 = R_8$ |
|---|---|---|---|---|
| XVI | $CD_3$ | $CH_3$ | H | H. |

18. A composition comprising a deuterium enriched composition of a compound according to claim 1 or any salts, esters or anhydrides thereof.

19. A method of treating a disease, condition, symptom or disorder associated with Metabolic Syndrome in a subject, said method comprising administering to said subject an effective amount of at least one deuterium enriched composition as defined in claim 1.

20. A method according to claim 19, wherein said disease, condition or disorder associated with Metabolic Syndrome is selected from dyslipidemia, diabetes, obesity, cancer, hypertension and neurodegeneration.

21. A deuterium enriched composition of a compound according to claim 1, wherein said compound is 2,2,15,15-tetramethyl(D12)-hexadecanedioic acid or any salt, ester or anhydride thereof.

22. A deuterium enriched composition of a compound according to claim 1, wherein said compound is 2,2,17,17-tetramethyl(D12)-octadecanedioic acid or any salt, ester or anhydride thereof.

23. An isolated deuterium enriched compound of general formula (I):

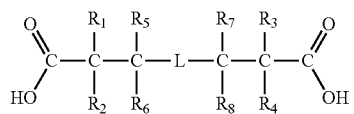

wherein each of $R_1$-$R_4$ is independently $CD_3$ and each of $R_5$-$R_8$ is independently hydrogen and L is a straight $C_{12}$ alkyl chain, which is 2,2,15,15-tetramethyl(D12)-hexadecanedioic acid or any salt, ester or anhydride thereof.

24. An isolated deuterium enriched compound of general formula (I):

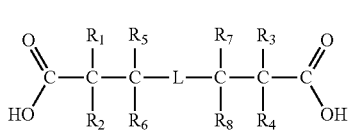

wherein each of $R_1$-$R_4$ is independently $CD_3$ and each of $R_5$-$R_8$ is independently hydrogen and L is a straight $C_{14}$ alkyl chain, which is 2,2,17,17-tetramethyl(D12)-octadecanedioic acid or any salt, ester or anhydride thereof.

25. A deuterium-enriched composition according to claim 1 wherein D at a specified position in the compound indicates at least 50.1% incorporation of deuterium at that position in the composition.

* * * * *